United States Patent
Schepis et al.

(12)

(10) Patent No.: US 12,279,871 B2
(45) Date of Patent: Apr. 22, 2025

(54) ELECTRODE ARRAY FOR SPATIALLY RANDOM ELECTRICAL STIMULATION

(71) Applicant: Soin Neuroscience, LLC, Dayton, OH (US)

(72) Inventors: Eric A. Schepis, Alpharetta, GA (US); Amol Soin, Dayton, OH (US)

(73) Assignee: Soin Neuroscience, LLC, Dayton, OH (US)

( * ) Notice: Subject to any disclaimer, the term of this patent is extended or adjusted under 35 U.S.C. 154(b) by 0 days.

(21) Appl. No.: 17/984,062

(22) Filed: Nov. 9, 2022

(65) Prior Publication Data

US 2024/0148300 A1    May 9, 2024

(51) Int. Cl.
     *A61N 1/36*      (2006.01)
     *A61B 5/24*      (2021.01)
     (Continued)

(52) U.S. Cl.
     CPC .............. *A61B 5/24* (2021.01); *A61N 1/0472* (2013.01); *A61N 1/36128* (2013.01); *G16H 40/63* (2018.01)

(58) Field of Classification Search
None
See application file for complete search history.

(56) References Cited

U.S. PATENT DOCUMENTS 5,983,141 A    11/1999   Sluijter et al.
7,117,038 B1   10/2006   Overstreet
(Continued)

FOREIGN PATENT DOCUMENTS

CN    101390789 A    3/2009
CN    101583879 A   11/2009
(Continued)

OTHER PUBLICATIONS

International Search Report, European Patent Office, International Patent Application No. PCT/US2018/013700, Mar. 19, 2018, 4 pages.

(Continued)

*Primary Examiner* — Erica S Lee
(74) *Attorney, Agent, or Firm* — Taft Stettinius & Hollister LLP

(57) ABSTRACT

An electrical stimulation system for delivering spatially random electrical stimulation to a patient through an electrode array according to one embodiment includes an electrode array comprising a plurality of electrodes spaced apart from one another, a signal generator electrically coupled to the electrode array and configured to deliver an electrical stimulation signal, and a controller comprising a processor and a memory having a plurality of instructions stored thereon that, in response to execution by the processor, causes the controller to randomly select an electrical configuration from the plurality of electrodes of the electrode array by randomly selecting a first set of electrodes of the plurality of electrodes to function as electrical sources and a second set of electrodes of the plurality of electrodes to function as electrical sinks, and to instruct the signal generator to deliver the electrical stimulation signal to the patient via the randomly selected electrical configuration.

19 Claims, 24 Drawing Sheets

(51) Int. Cl.
*A61N 1/04* (2006.01)
*A61N 1/05* (2006.01)
*G16H 40/63* (2018.01)

(56) References Cited

U.S. PATENT DOCUMENTS

| | | | |
|---|---|---|---|
| 10,603,498 B2 | 3/2020 | Blum et al. | |
| 11,420,054 B2* | 8/2022 | Page | A61N 1/36014 |
| 2003/0114886 A1 | 6/2003 | Gluckman et al. | |
| 2006/0149337 A1 | 7/2006 | John | |
| 2006/0161235 A1* | 7/2006 | King | A61N 1/0553 |
| | | | 607/117 |
| 2007/0060991 A1* | 3/2007 | North | A61N 1/0553 |
| | | | 607/117 |
| 2007/0142864 A1 | 6/2007 | Libbus et al. | |
| 2008/0077192 A1* | 3/2008 | Harry | A61N 1/0476 |
| | | | 42/84 |
| 2008/0269836 A1 | 10/2008 | Foffani et al. | |
| 2009/0030476 A1 | 1/2009 | Hargrove | |
| 2010/0010556 A1 | 1/2010 | Zhao et al. | |
| 2011/0009919 A1 | 1/2011 | Carbunaru et al. | |
| 2011/0009923 A1 | 1/2011 | Lee | |
| 2011/0144521 A1 | 6/2011 | Molnar et al. | |
| 2011/0201944 A1 | 8/2011 | Higgins et al. | |
| 2012/0016447 A1 | 1/2012 | Zhu et al. | |
| 2012/0059438 A1 | 3/2012 | De Ridder | |
| 2012/0123502 A1 | 5/2012 | Aghassian et al. | |
| 2013/0245486 A1 | 9/2013 | Simon et al. | |
| 2013/0253365 A1 | 9/2013 | Crosson et al. | |
| 2013/0289645 A1* | 10/2013 | Pei | A61N 1/371 |
| | | | 607/28 |
| 2013/0317564 A1 | 11/2013 | Lin et al. | |
| 2014/0031895 A1 | 1/2014 | Rahimi et al. | |
| 2014/0067022 A1* | 3/2014 | Carcieri | G16Z 99/00 |
| | | | 607/62 |
| 2014/0316268 A1 | 10/2014 | Kafiluddi et al. | |
| 2015/0012063 A1 | 1/2015 | Chen | |
| 2015/0157864 A1 | 6/2015 | Rosenberg | |
| 2016/0001083 A1* | 1/2016 | Moffitt | A61N 1/372 |
| | | | 607/62 |
| 2016/0074651 A1 | 3/2016 | Moffitt et al. | |
| 2016/0199662 A1* | 7/2016 | Wundrich | A61N 1/0484 |
| | | | 607/45 |
| 2016/0256689 A1 | 9/2016 | Vallejo et al. | |
| 2016/0271413 A1 | 9/2016 | Vallejo et al. | |
| 2017/0001003 A1 | 1/2017 | Pivonka et al. | |
| 2019/0201657 A1 | 7/2019 | Popelka et al. | |
| 2019/0298988 A1* | 10/2019 | Monteiro | A61N 1/0539 |
| 2019/0366097 A1 | 12/2019 | Schepis | |
| 2020/0054879 A1* | 2/2020 | Torgerson | A61B 5/686 |
| 2020/0078593 A1* | 3/2020 | Zhu | A61N 1/37247 |
| 2020/0107940 A1 | 4/2020 | Murphy et al. | |
| 2020/0139127 A1* | 5/2020 | Zhang | A61N 1/36071 |
| 2020/0164213 A1 | 5/2020 | John | |
| 2020/0179698 A1 | 6/2020 | Schepis et al. | |
| 2020/0254257 A1 | 8/2020 | Liu et al. | |
| 2020/0353256 A1 | 11/2020 | Vallejo et al. | |
| 2021/0387004 A1* | 12/2021 | Single | A61N 1/36125 |
| 2022/0080200 A1* | 3/2022 | Molnar | A61N 1/36071 |
| 2022/0096822 A1 | 3/2022 | Schepis et al. | |
| 2022/0257957 A1* | 8/2022 | Kotchevar | A61N 1/04 |
| 2022/0288394 A1* | 9/2022 | Bennett | A61N 1/36057 |
| 2023/0018108 A1* | 1/2023 | Hunsberger | A61N 1/0556 |
| 2023/0074017 A1* | 3/2023 | Pan | A61N 1/36125 |
| 2023/0146551 A1* | 5/2023 | Park | A61N 1/36196 |
| | | | 607/73 |

FOREIGN PATENT DOCUMENTS

| | | | |
|---|---|---|---|
| EP | 2703042 A1 | 3/2014 | |
| JP | 2006204520 A | 8/2006 | |
| JP | 2009505689 A | 2/2009 | |
| WO | 9318821 A1 | 9/1993 | |

OTHER PUBLICATIONS

Written Opinion, European Patent Office, International Patent Application No. PCT/US2018/013700, Mar. 19, 2018, 7 pages.
Australian First Examination Report; Australia Patent Office; Australian Patent Application No. 2018210216; Aug. 23, 2019; 2 pages.
Canadian Office Action; Canadian Intellectual Property Office; Canadian Patent Application No. 3,048,498; Jan. 29, 2020; 5 pages.
Japanese Office Action; Japan Patent Office; Japanese Patent Application No. 2019-538339; Dec. 10, 2019; 14 pages.
Korean Office Action; Korean Intellectual Property Office; Korean Patent Application No. 10-2019-7023751; Nov. 14, 2019; 4 pages.
New Zealand First Examination Report; New Zealand Intellectual Property Office; New Zealand Patent Application No. 756351; Feb. 10, 2020; 3 pages.
International Search Report; International Searching Authority; International Application No. PCT/US2023/011998; Apr. 12, 2023; 2 pages.
Written Opinion of the International Searching Authority; International Searching Authority; International Application No. PCT/US2023/011998; Apr. 12, 2023; 9 pages.
Canadian Examination Report; Canadian Intellectual Property Office; Canadian Patent Application No. 3,048,495; Aug. 10, 2020; 5 pages.
Chinese Office Action; China National Intellectual Property Administration; Chinese Patent Application No. 201880007499.5; Oct. 10, 2022; 7 pages.
Indian Examination Report; Intellectual Property India; Indian Patent Application No. 201917031620; Jan. 27, 2021; 5 pages.
Japanese Office Action; Japan Patent Office; Japanese Patent Application No. 2019-538339; Sep. 1, 2020; 7 pages.
New Zealand Second Examination Report; New Zealand Intellectual Property Office; New Zealand Patent Application No. 756351; Jul. 14, 2020; 4 pages.
New Zealand Third Examination Report; New Zealand Intellectual Property Office; New Zealand Patent Application No. 756351; Nov. 3, 2020; 1 page.
International Search Report, International Searching Authority, International Patent Application No. PCT/US23/79233, Apr. 15, 2024, 2 pages.
Written Opinion of the International Searching Authority, International Searching Authority, International Patent Application No. PCT/US23/79233, Apr. 15, 2024, 7 pages.

* cited by examiner

ELECTRODE ARRAY FOR SPATIALLY RANDOM ELECTRICAL STIMULATION

BACKGROUND

Electrical stimulation technologies are used to mitigate pain and other conditions. The technologies work by delivering electrical stimulation to the various parts of the nervous system (e.g., sensory receptors, peripheral nerves, spinal cord, and brain). For example, the stimulation devices used today deliver pulsed periodic waveforms through electrical contacts that are positioned overtop of the dorsal columns of the spinal cord, dorsal root ganglion, or long peripherals nerves. The electrical contacts that are used for stimulation are chosen at the onset of the treatment and maintained throughout the duration of the therapy, which may last for years. Although the technologies used today cause a moderate reduction in pain intensity in the majority of the persons treated, the effects of the stimulation often decline after a few years of use. This phenomenon is known as neurological tolerance (or accommodation), and it is the leading cause of stimulator removal. Electrical stimulation technologies are used to treat a variety of disease states, such as chronic pain, overactive bladder, movement disorders, and cardiovascular disease. However, the treatment effects and time-course are limited.

SUMMARY

One embodiment is directed to a unique system and method for delivering spatially random electrical stimulation to a patient through an electrode array. Other embodiments are directed to apparatuses, systems, devices, hardware, methods, and combinations thereof for delivering spatially random electrical stimulation to a patient through an electrode array.

According to an embodiment, an electrical stimulation system for delivering spatially random electrical stimulation to a patient through an electrode array may include an electrode array comprising a plurality of electrodes spaced apart from one another, a signal generator electrically coupled to the electrode array and configured to deliver an electrical stimulation signal, and a controller comprising a processor and a memory having a plurality of instructions stored thereon that, in response to execution by the processor, causes the controller to randomly select an electrical configuration from the plurality of electrodes of the electrode array, wherein to randomly select the electrical configuration includes to randomly select a first set of electrodes of the plurality of electrodes to function as electrical sources and a second set of electrodes of the plurality of electrodes, different from the first set of electrodes, to function as electrical sinks, and instruct the signal generator to deliver the electrical stimulation signal to the patient via the randomly selected electrical configuration.

In some embodiments, the first set of electrodes may include a first number of electrodes and the second set of electrodes may include a second number of electrodes different from the first number.

In some embodiments, the plurality of electrodes may include a third set of electrodes of a first cross-sectional shape and a fourth set of electrodes of a second cross-sectional shape different from the first cross-sectional shape.

In some embodiments, the first cross-sectional shape may be a circular shape.

In some embodiments, the plurality of electrodes may include a third set of electrodes of a first size and a fourth set of electrodes of a second size greater than the first size.

In some embodiments, the signal generator may be configured to deliver low-frequency signal components through only the fourth set of electrodes.

In some embodiments, the plurality of electrodes may include a third set of electrodes and a fourth set of electrodes different from the third set of electrodes, and to instruct the signal generator to deliver the electrical stimulation signal to the patient via the randomly selected electrical configuration may include to instruct the signal generator to deliver a first set of features of the electrical stimulation signal to the patient via the third set of electrodes and a second set of features of the electrical stimulation signal, different from the first set of features, to the patient via the fourth set of electrodes.

In some embodiments, the first set of features may include one or more of a frequency range of the electrical stimulation signal or an amplitude range of the electrical stimulation signal.

In some embodiments, the electrical stimulation system may further include an electrode assembly that includes the plurality of electrodes, the third set of electrodes may be positioned on the electrode assembly at a first section of the electrode assembly, and the fourth set of electrodes may be positioned on the electrode assembly at a second section of the electrode assembly different from the first section.

In some embodiments, each of the third set of electrodes and the fourth set of electrodes may be selected based on one or more of an electrode size, an electrode material, or an electrode location on an electrode assembly.

In some embodiments, the plurality of electrodes may include a third set of electrodes composed of a first material and a fourth set of electrodes composed of a second material different from the first material.

In some embodiments, the plurality of instructions may further cause the controller to randomly assign a polarity to one or more of the electrodes of the first set of electrodes and the second set of electrodes.

In some embodiments, the electrode array may include at least a distal section and a proximal section, and the signal generator may be configured to deliver high-frequency signal components through only the distal section of the electrode array.

In some embodiments, the electrode array may include at least a distal section and a proximal section, and the signal generator may be configured to amplify signals transmitted through the distal section at a different weight from signals transmitted through the proximal section.

In some embodiments, the electrical stimulation signal may include or be embodied as a noise signal.

In some embodiments, the plurality of instructions may further cause the controller to partition a frequency range of the electrical stimulation signal into a plurality of discrete frequency bands, each of the discrete frequency bands having a corresponding bandwidth, adjust an amplitude of one or more of a voltage or a current of the electrical stimulation signal within a selected frequency band of the plurality of discrete frequency bands to generate an adjusted electrical signal based on feedback received from the patient, and instruct the signal generator to deliver the adjusted electrical signal to the patient via the randomly selected electrical configuration.

In some embodiments, the feedback may include at least one of feedback received from the patient as patient self-report regarding the therapy delivered to the patient, feedback based on data generated by one or more sensors of the electrical stimulation system, wherein the one or more sensors measure one or more physiological outcomes of the patient, or feedback data received from a machine learning system.

In some embodiments, the frequency range of the electrical stimulation signal may be 0.05 Hz to 2 kHz.

In some embodiments, the frequency range of the electrical stimulation signal may be 1 kHz to 100 kHz.

In some embodiments, the frequency range of the electrical stimulation signal may be 100 kHz to 1 MHz.

In some embodiments, the plurality of instructions may further cause the controller to randomly select a new electrical configuration from the plurality of electrodes of the electrode array in response to a determination that a threshold has been met.

In some embodiments, the threshold may be defined as a predefined period of time elapsed since randomly selecting the electrical configuration.

In some embodiments, the threshold may be associated with one or more characteristics of the spatially random electrical stimulation being delivered to the patient.

According to another embodiment, a method of delivering spatially random electrical stimulation to a patient through an electrode array that includes a plurality of electrodes may include randomly selecting, by an electrical stimulation system, an electrical configuration from the plurality of electrodes of the electrode array, wherein randomly selecting the electrical configuration includes randomly selecting a first set of electrodes of the plurality of electrodes to function as electrical sources and a second set of electrodes of the plurality of electrodes, different from the first set of electrodes, to function as electrical sinks, and delivering, by the electrical stimulation system, an electrical stimulation signal to the patient via the randomly selected electrical configuration.

In some embodiments, the method may further include partitioning, by the electrical stimulation system, a frequency range of the electrical stimulation signal into a plurality of discrete frequency bands, each of the discrete frequency bands having a corresponding bandwidth, and adjusting, by the electrical stimulation system, an amplitude of one or more of a voltage or a current of the electrical stimulation signal within a selected frequency band of the plurality of discrete frequency bands to generate an adjusted electrical signal based on feedback received from the patient, wherein delivering the electrical stimulation signal to the patient includes delivering the adjusted electrical signal to the patient via the randomly selected electrical configuration.

In some embodiments, the feedback may include at least one of feedback received from the patient as patient self-report regarding the therapy delivered to the patient, feedback based on data generated by one or more sensors of the electrical stimulation system, wherein the one or more sensors measure one or more physiological outcomes of the patient, or feedback data received from a machine learning system.

In some embodiments, the first set of electrodes may include a first number of electrodes and the second set of electrodes may include a second number of electrodes different from the first number.

In some embodiments, the plurality of electrodes may include a third set of electrodes of a first cross-sectional shape and a fourth set of electrodes of a second cross-sectional shape different from the first cross-sectional shape.

In some embodiments, the plurality of electrodes may include a third set of electrodes of a first size and a fourth set of electrodes of a second size greater than the first size.

In some embodiments, the plurality of electrodes may include a third set of electrodes composed of a first material and a fourth set of electrodes composed of a second material different from the first material.

This summary is not intended to identify key or essential features of the claimed subject matter, nor is it intended to be used as an aid in limiting the scope of the claimed subject matter. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
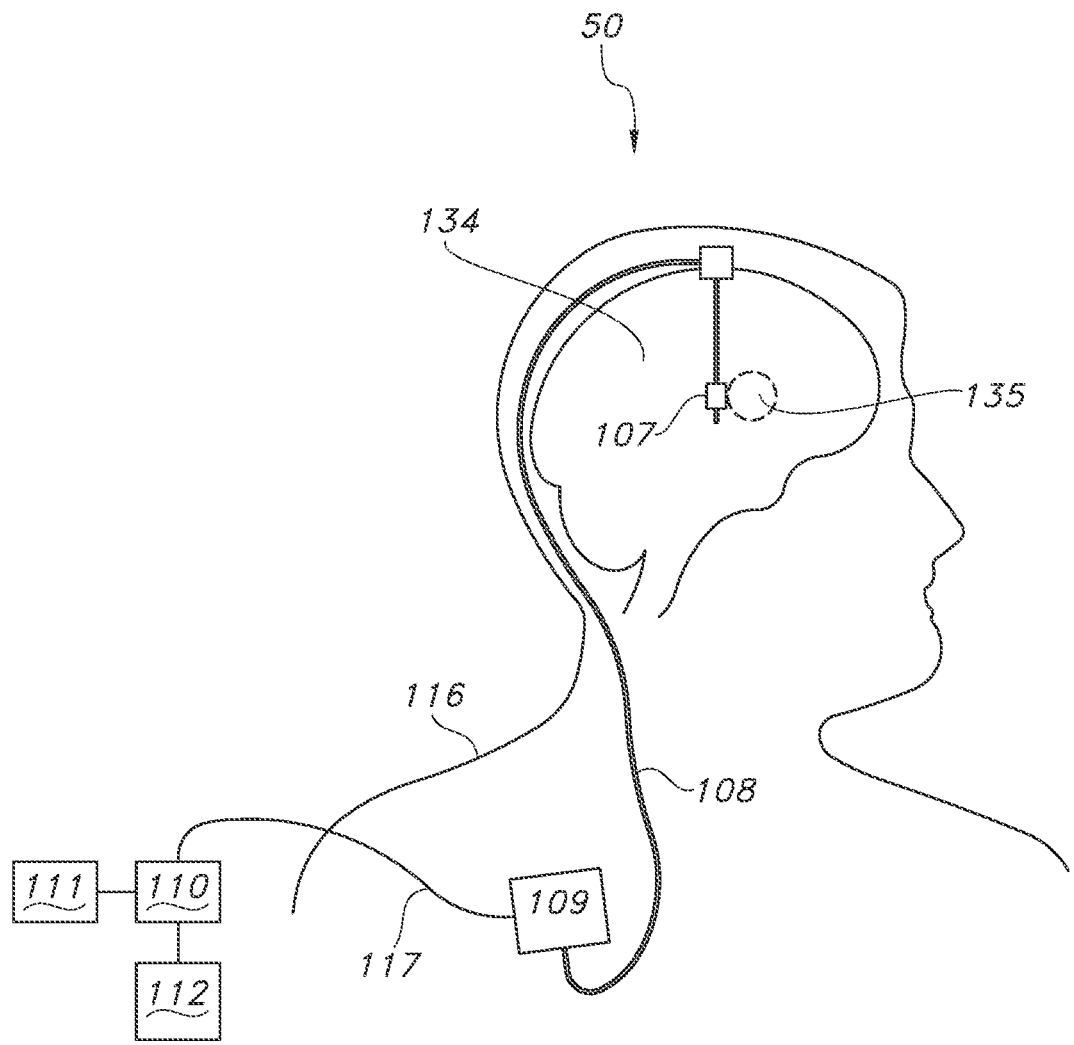
FIG. 1 illustrates at least one embodiment of a system for delivering one or more electrical signals to target neural tissue, non-neural tissue, or a combination thereof in a patient, where the target tissue is located within or adjacent to the patient's brain.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

As described above, existing electrical stimulation technologies are inhibited from long-term efficacy due to the patient often developing neurological tolerance (or accommodation) to the stimulation. It should be appreciated that the technologies described herein include an electrical stimulation system that delivers electrical stimuli in a random fashion through a set of electrodes (e.g., electrical contacts) to neural and/or non-neural tissue, which has been found to be more effective at treating acute and chronic pain and other medical disorders than existing technologies. For example, in illustrative embodiments, the electrical stimulation system includes an electrode array that delivers spatially random electrical stimulation to the patient, which can avoid delivering a repetitive barrage of electrical stimulation to the same biological tissue and thereby avoid eliciting neurological tolerance in the patient.

As described in greater detail below, the therapy may be generated by an external or implantable electrical stimulator and delivered through electrodes (e.g., an electrode array) to the patient's brain or spinal cord, a dorsal root ganglion, a sympathetic nerve or chain ganglion, a cranial nerve, a parasympathetic nerve, or a peripheral nerve. The therapy may be used to treat pain (e.g., chronic pain), an autonomic disorder (e.g., diabetic peripheral neuropathy, hypertension, hypotension, complex regional pain syndrome (CRPS), Raynaud's syndrome, overactive bladder, urinary incontinence, fecal incontinence, fecal constipation, migraine, etc.), a sensory disorder (e.g., tinnitus, hearing loss, vertigo, etc.), a motor disorder (e.g., Huntington's disease, Parkinson's disease, Multiple Sclerosis, spinal muscular atrophy (SMA), dystonia, essential tremor, etc.), or a combination thereof. Further, the therapy provided to the patient can elicit plastic changes in neural tissue, non-neural tissue, or a combination thereof to mitigate or abolish a pathophysiologic disease or syndrome. Plastic changes are changes to the neural tissue, non-neural tissue, or a combination thereof in response to physiological demands. Such plastic changes can include morphological and functional changes.

Whether the electrical signal(s) are being applied to target neural tissue, non-neural tissue, or a combination thereof located within or adjacent the patient's brain or spinal cord, a dorsal root ganglion, a sympathetic chain ganglion, a cranial nerve, autonomic circuitry, or a peripheral nerve, the technologies described herein illustrate that the specific electrical configuration of the electrode array, the specific parameters of the electrical signals, and/or the location of the electrode array though which electrical signals are delivered can be selectively controlled to provide improved symptom relief and therapy to the patient for the treatment of pain, autonomic disorders, sensory disorders, motor disorders, etc. Additionally, the specific physical design of the electrode array may be selected. The specific system and parameters are discussed in more detail below.

Referring now to FIG. 1, there is illustrated a system 50 for delivering one or more electrical signals to provide therapy to a patient 116, where the target neural tissue, non-neural tissue, or a combination thereof 135 is located within or adjacent tissue within the patient's brain 134. In general, the system 50 in FIG. 1 can include one or more electrodes 107 (shown diagrammatically in FIG. 1) that are connected by an electrical lead 108 to a signal generator 109. As described herein, multiple electrodes 107 may be arranged into an electrode array in some embodiments (see, e.g., FIGS. 11-18). In various embodiments, one or more electrodes 107 (or electrical contacts) may be embodied on, form a portion of, or be electrically coupled to one or more electrical leads 108 that are electrically (or electromagnetically) coupled to the signal generator 109. An additional lead 117 can be used to couple the signal generator 109 to the rest of the system 50, which can include a user interface 112 and a controller 110, where it is to be understood that as an alternative to the use of the lead 117, the signal generator 109 can be wirelessly connected to the rest of the system 50. The system 50 can also include a power system 111 and/or a patient monitor system. Further, it should be understood that while the system 50 of FIG. 1 illustrates a configuration where electrical signals can be delivered to target neural tissue, non-neural tissue, or a combination 135 thereof utilizing one or more electrodes 107 (e.g., an electrode array) coupled to an implantable signal generator 109 via a lead 108, the electrode(s) 107 can alternatively be coupled to an external signal generator via a wireless antenna system. It should be appreciated that, in some embodiments, more than one electrode 107, more than one electrical lead 108, and/or more than one signal generator 109 may be used in the system 50. Regardless of the exact type (e.g., percutaneous, transcutaneous, implantable, etc.) or configuration (e.g., monopolar, bipolar, multipolar, etc.) of the electrode(s) 107, the electrode(s) 107 can be in the form of an electrode assembly that can deliver electrical signals to a patient to provide therapy to the patient and/or improve one or more of the patient's symptoms. Specific diseases or conditions that can be treated based on stimulation of the brain include, for example, Parkinson's disease, essential tremor, depression, obsessive compulsive disorder, Tourette's syndrome, epilepsy, schizophrenia, narcolepsy, seizures, Alzheimer's disease, tinnitus, Meniere's disease, and chronic pain.

Figure 2:
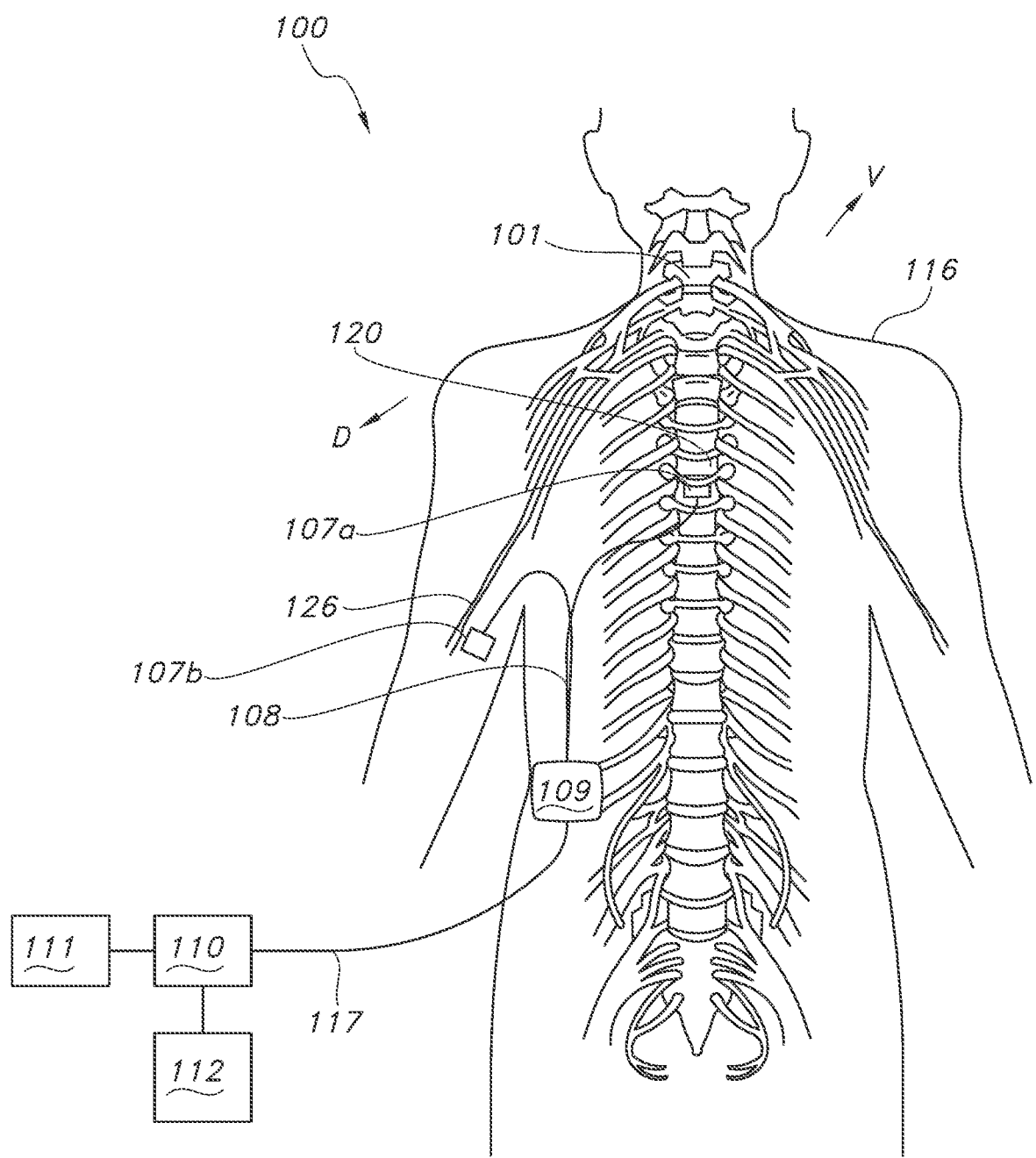
FIG. 2 illustrates at least one embodiment of a system for delivering one or more electrical signals to target neural tissue, non-neural tissue, or a combination thereof in a patient, where the target tissue is located within or adjacent the spinal cord.

Referring now to FIG. 2, there is illustrated a system 100 for delivering one or more electrical signals to provide therapy to a patient, where the target neural tissue, non-neural tissue, or a combination thereof is located within or adjacent the spinal cord 101 of a patient 116. As shown in FIG. 2, the system 100 can include multiple devices to control and deliver electrical signals to one or more areas of target neural tissue, non-neural tissue, or a combination thereof located within or adjacent the spinal cord 101 to provide therapy to a patient 116. In general, the system 100 in FIG. 2 can include one or more electrodes 107a and/or 107b that are connected by one or more electrical leads 108 to a signal generator 109. As described herein, multiple electrodes 107 may be arranged into an electrode array in some embodiments (see, e.g., FIGS. 11-18). An additional lead 117 can be used to couple the signal generator 109 to other components of the system 100, which can include a user interface 112 and a controller 110, where it is to be understood that as an alternative to the use of the lead 117, the signal generator 109 can be wirelessly connected to the rest of the system 50. The system can also include an isolated power system 111 and/or a patient monitor system. Further, it should be understood that while the system 100 of FIG. 2 illustrates a configuration where electrical signals can be delivered to target neural tissue, non-neural tissue, or a combination thereof utilizing electrodes 107a and/or 107b coupled to an implantable signal generator 109 via a lead 108, the electrodes 107a and/or 107b can alternatively be coupled to an external signal generator via a wireless antenna system. Regardless, the electrodes 107a and/or 107b can be in the form of an electrode assembly that can deliver electrical signals to a patient to provide therapy to the patient and/or improve one or more of the patient's symptoms based on, for example, the specific location of the electrodes, as discussed in more detail in FIGS. 3-7 below.

Figure 3:
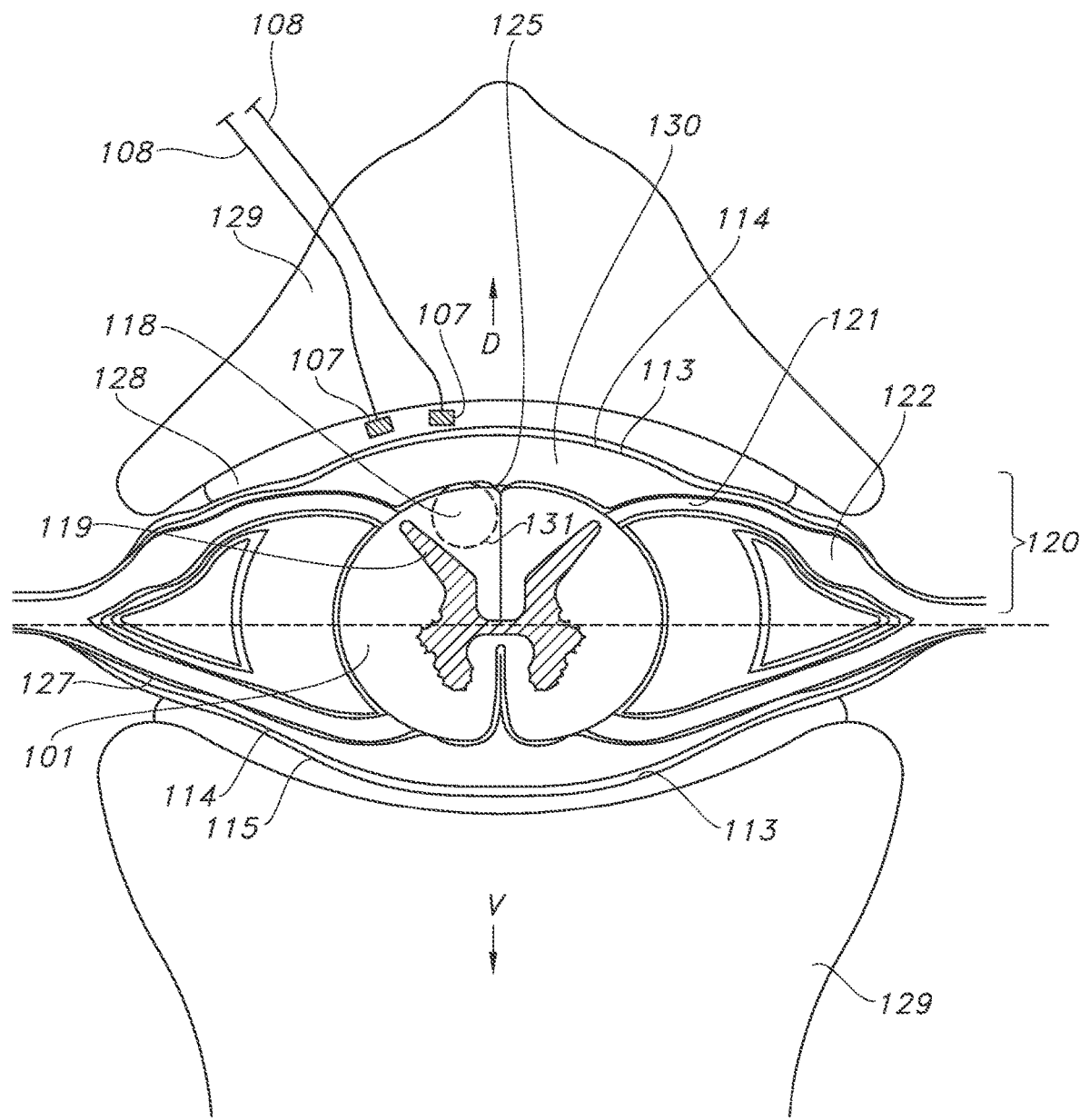
FIG. 3 is a zoomed-in view of the spinal cord and illustrates at least one option for electrode placement according to the system of FIG. 2, where the target tissue is located within or adjacent a dorsal region of the spinal cord, such as the dorsal columns.

Referring now to FIG. 3, the placement of the electrode or electrodes 107 (e.g., electrode array) in order to deliver one or more electrical signals to an area within or adjacent target neural tissue, non-neural tissue, or a combination thereof 131 located adjacent a dorsal region 120 of the spinal cord 101, and in particular a dorsal column 118, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal region 120 of the spinal cord 101, where the dorsal region 120 of the spinal cord 101 can be identified via locating the posterior median sulcus 125. As shown, the epidural space 128 is positioned between the bone 129 (vertebrae) and the dura mater 115. Thus, electrical signals transmitted by the electrode(s) 107 must be configured to pass through the dura mater 115, subdural cavity 113, arachnoid mater 114, subarachnoid cavity 130, and pia mater 127 to reach the target neural tissue, non-neural tissue, or a combination thereof 131 and deliver the desired electrical signals therein. By placing the electrode or electrodes 107 in the epidural space 128 adjacent a dorsal region 120 of the spinal cord 101, electrical signals can be delivered to target neural tissue, non-neural tissue, or a combination thereof 131 located within or adjacent a dorsal column 118 to provide therapy to the patient. It is also to be understood that the electrode or electrodes 107 can be positioned in any suitable location in the dorsal region 120 of the spinal cord 101 in order to deliver electrical signals to an area within or adjacent other target neural tissue, non-neural tissue, or a combination thereof, such as tissue located adjacent a dorsal horn 119 or a dorsal root 121. Specific diseases or conditions that can be treated based on stimulation of the dorsal region of the spinal cord, and in particular, the dorsal columns include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 4:
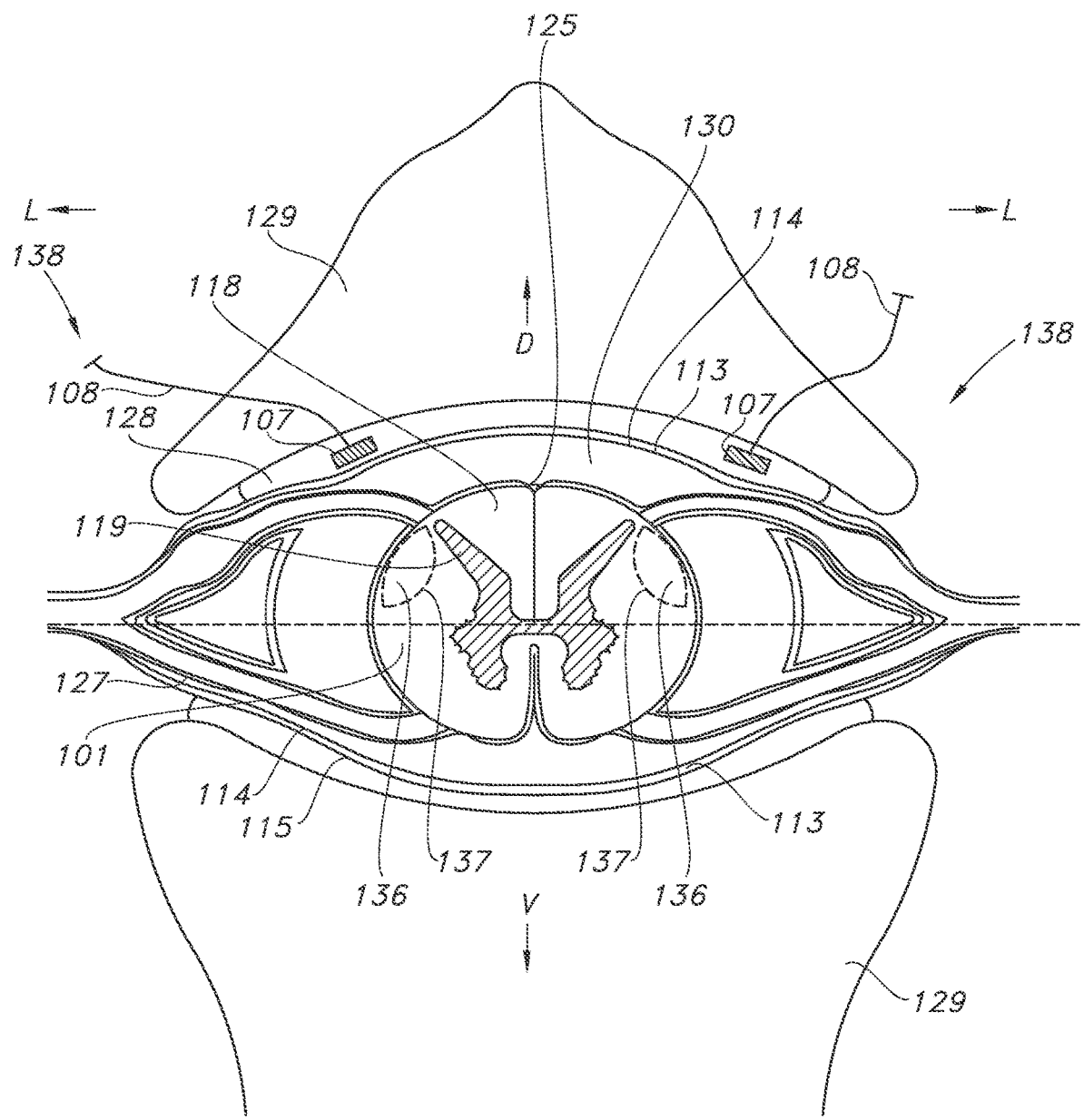
FIG. 4 is a zoomed-in view of the spinal cord and illustrates at least one other option for electrode placement according to the system of FIG. 2, where the target tissue is located within or adjacent to the dorsolateral region of the spinal cord, such as the dorsolateral funiculus.

Referring now to FIG. 4, the placement of the electrode or electrodes 107 (e.g., an electrode array) in order to deliver one or more electrical signals to an area within or adjacent target neural tissue, non-neural tissue, or a combination thereof 137 located in a dorsolateral region 138 of the spinal cord 101 is discussed in more detail, where the dorsal D, ventral V, and lateral L directions are labeled for reference purposes. For instance, one or more electrodes 107 can be positioned adjacent a dorsolateral region 138 of the spinal cord 101. By placing the electrode or electrodes 107 adjacent a dorsolateral region 138 of the spinal cord 101, electrical signals can be delivered to target neural tissue, non-neural tissue, or a combination thereof 137 located within or adjacent a dorsolateral region 138 of the spinal cord 101 to provide therapy to the patient. Specifically, nerve fiber activity in the right or left dorsolateral funiculus 136 or a combination thereof can be altered via electrical signals in order to treat or alleviate symptoms associated various conditions. Specific diseases or conditions that can be treated based on stimulation of the dorsolateral region of the spinal cord, and in particular, the dorsolateral funiculus include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 5:
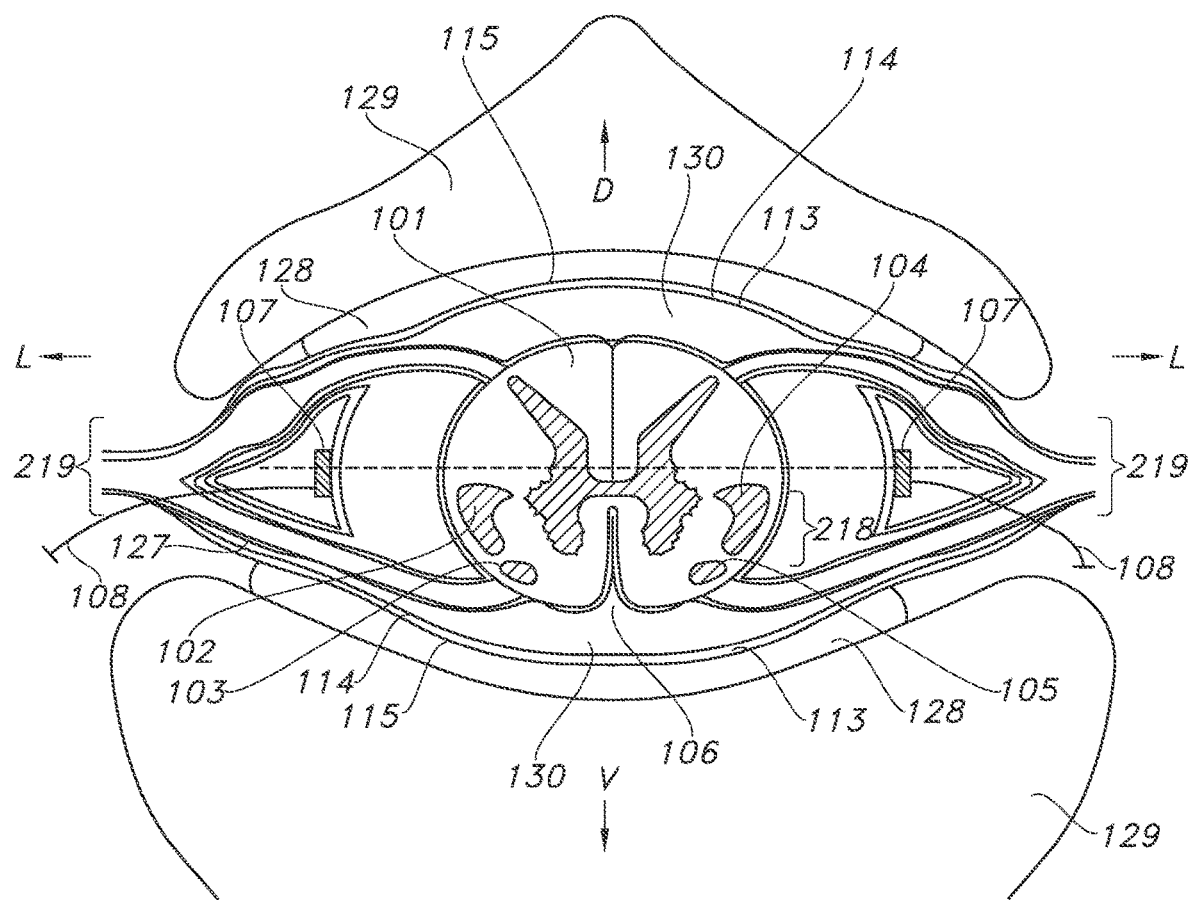
FIG. 5 is a zoomed-in view of the spinal cord and illustrates at least one other option for electrode placement according to the system of FIG. 2, where the target tissue is located within or adjacent the lateral region of the spinal cord, such as the spinothalamic tract.

Referring now to FIG. 5, the placement of the electrode or electrodes 107 (e.g., an electrode array) in order to deliver one or more electrical signals to an area within or adjacent target neural tissue, non-neural tissue, or a combination thereof 218 located in a lateral region 219 of the spinal cord 101 is discussed in more detail, where the dorsal D, ventral V, and lateral L directions are labeled for reference purposes. For instance, one or more electrodes 107 can be positioned adjacent a lateral region 219 of the spinal cord 101. By placing the electrode or electrodes 107 adjacent lateral region 219 of the spinal cord 101, electrical signals can be delivered to target neural tissue, non-neural tissue, or a combination thereof 218 located within or adjacent a lateral region 219 of the spinal cord 101 to provide therapy to the patient. Specifically, nerve fiber activity in the right lateral spinothalamic tract 102, the left lateral spinothalamic tract 104, or a combination thereof can be altered via electrical signals in order to treat or alleviate symptoms associated various conditions. Moreover, it is to be understood that nerve fiber activity in the right anterior spinothalamic tract 103, the left anterior spinothalamic tract 105, or a combination thereof can also be altered via electrical signals based on the specific positioning of the one or more electrodes 107. Specific diseases or conditions that can be treated based on stimulation of the lateral region of the spinal cord, and in particular, the lateral spinothalamic tract include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 6:
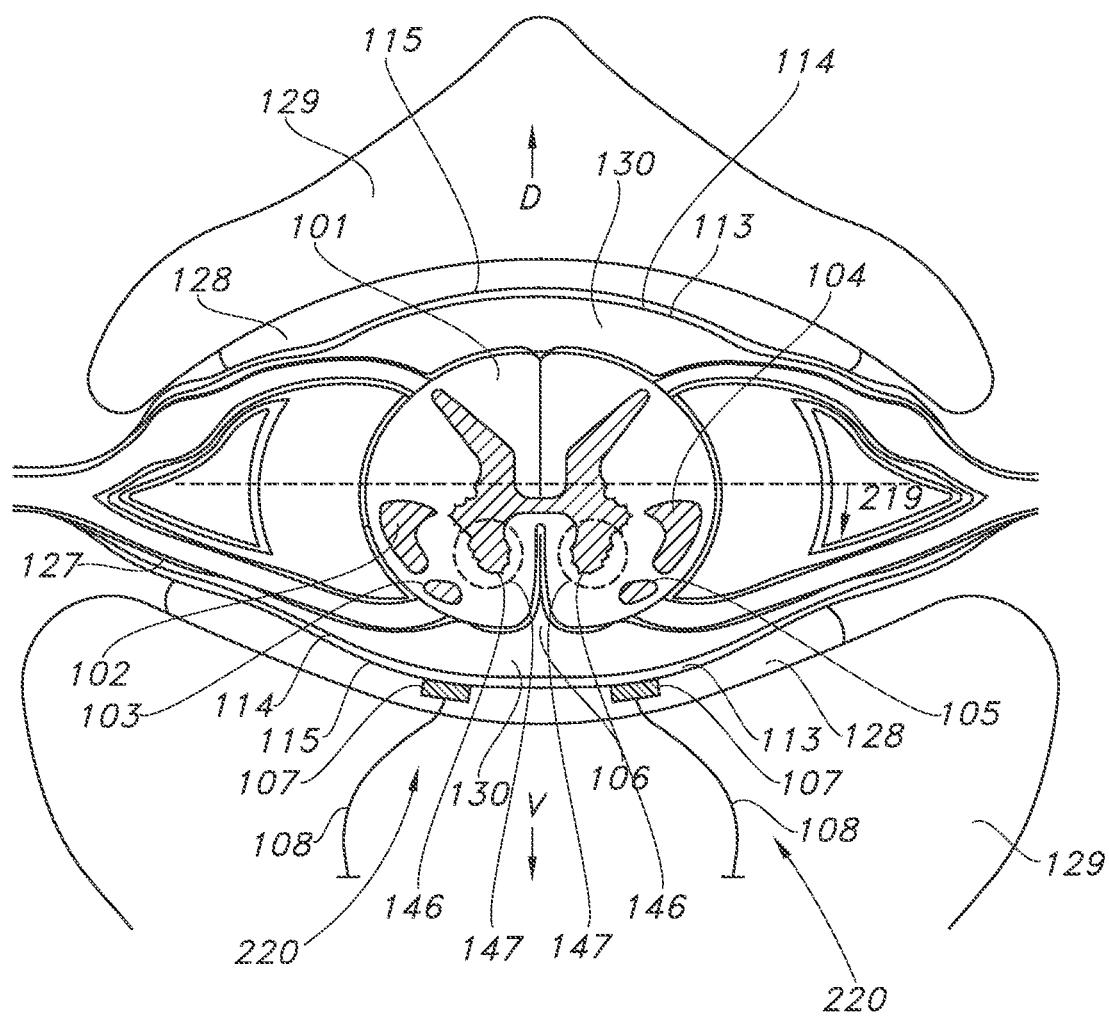
FIG. 6 is a zoomed-in view of the spinal cord and illustrates at least one other option for electrode placement according to the system of FIG. 2, where the target tissue is located with or adjacent the ventral region of the spinal cord, such as the ventral horn.

Referring now to FIG. 6, the placement of the electrode or electrodes 107 (e.g., an electrode array) in order to deliver one or more electrical signals to an area within or adjacent target neural tissue, non-neural tissue, or a combination thereof 147 located in a ventral region 220 of the spinal cord 101 is discussed in more detail, where the dorsal D and ventral V directions are labeled for reference purposes. For instance, one or more electrodes 107 can be positioned within a portion of the epidural space 128 of the patient 116 adjacent a ventral region 220 of the spinal cord 101, where the ventral region 220 of the spinal cord 101 can be identified via locating the anterior median fissure 106. As shown, the epidural space 128 is positioned between the bone 129 (vertebrae) and the dura mater 115. Thus, electrical signals transmitted by the electrode(s) 107 are configured to pass through the dura mater 115, subdural cavity 113, arachnoid mater 114, subarachnoid cavity 130, and pia mater 127 to reach the target neural tissue, non-neural tissue, or a combination thereof 147 and deliver the desired electrical signals therein. By placing the electrode or electrodes 107 in the epidural space 128 adjacent a ventral region 220 of the spinal cord 101, electrical signals can be delivered to target neural tissue, non-neural tissue, or a combination thereof 147 located in a ventral region 220 of the spinal cord 101 to provide therapy to the patient. Specifically, in one particular embodiment, nerve fiber activity in the right or left ventral horn 146 or a combination thereof can be altered via electrical signals in order to treat or alleviate symptoms associated various conditions. Specific diseases or conditions that can be treated based on stimulation of the ventral region of the spinal cord include, for example, motoneuron disease (amyotrophic lateral sclerosis; progressive muscular atrophy; progressive bulbar palsy; primary lateral sclerosis; hereditary spastic paraplegia), spinal muscular atrophy (infantile and juvenile spinal muscular atrophy; focal amyotrophy), and multiple sclerosis.

Figure 7:
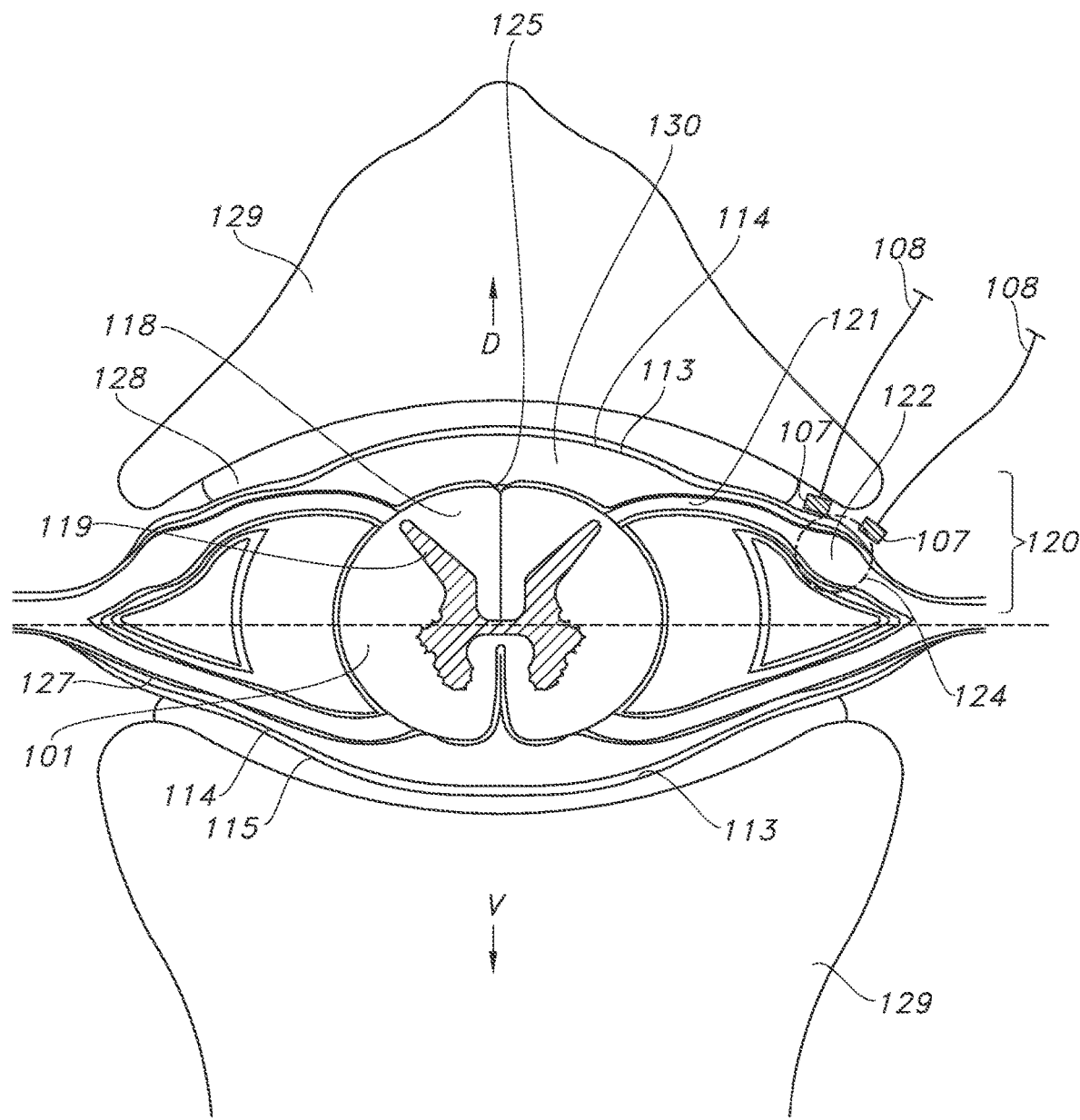
FIG. 7 is a zoomed-in view of the spinal cord and illustrates at least one other option for electrode placement according to the system of FIG. 2, where the target tissue is located within or adjacent a dorsal root ganglion.

Referring now to FIG. 7, the placement of the electrode or electrodes 107 (e.g., an electrode array) in order to deliver one or more electrical signals to an area within or adjacent target neural tissue, non-neural tissue, or a combination thereof 124 located adjacent or near a dorsal region 120 of the spinal cord 101, and in particular a dorsal root ganglion 122, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal (or posterior) portion 120 of the spinal cord 101, where the dorsal (or posterior) portion 120 of the spinal cord 101 can be identified via locating the posterior median sulcus 125. As shown, the epidural space 128 is positioned between the bone 129 (vertebrae) and the dura mater 115. Thus, electrical signals transmitted by the electrode(s) 107 are configured to pass through the dura mater 115, subdural cavity 113, arachnoid mater 114, subarachnoid cavity 130, and pia mater 127 to reach the target neural tissue, non-neural tissue, or a combination thereof 124 and deliver the desired electrical signals therein. By placing the electrode or electrodes 107 in the epidural space 128 adjacent a dorsal D (or posterior) portion 120 of the spinal cord 101, electrical signals can be delivered to target neural tissue, non-neural tissue, or a combination thereof 124 located within or adjacent a dorsal root ganglion 122 to provide therapy to the patient. Specific diseases or conditions that can be treated based on stimulation of the dorsal root ganglion include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain and fibromyalgia.

Figure 8:
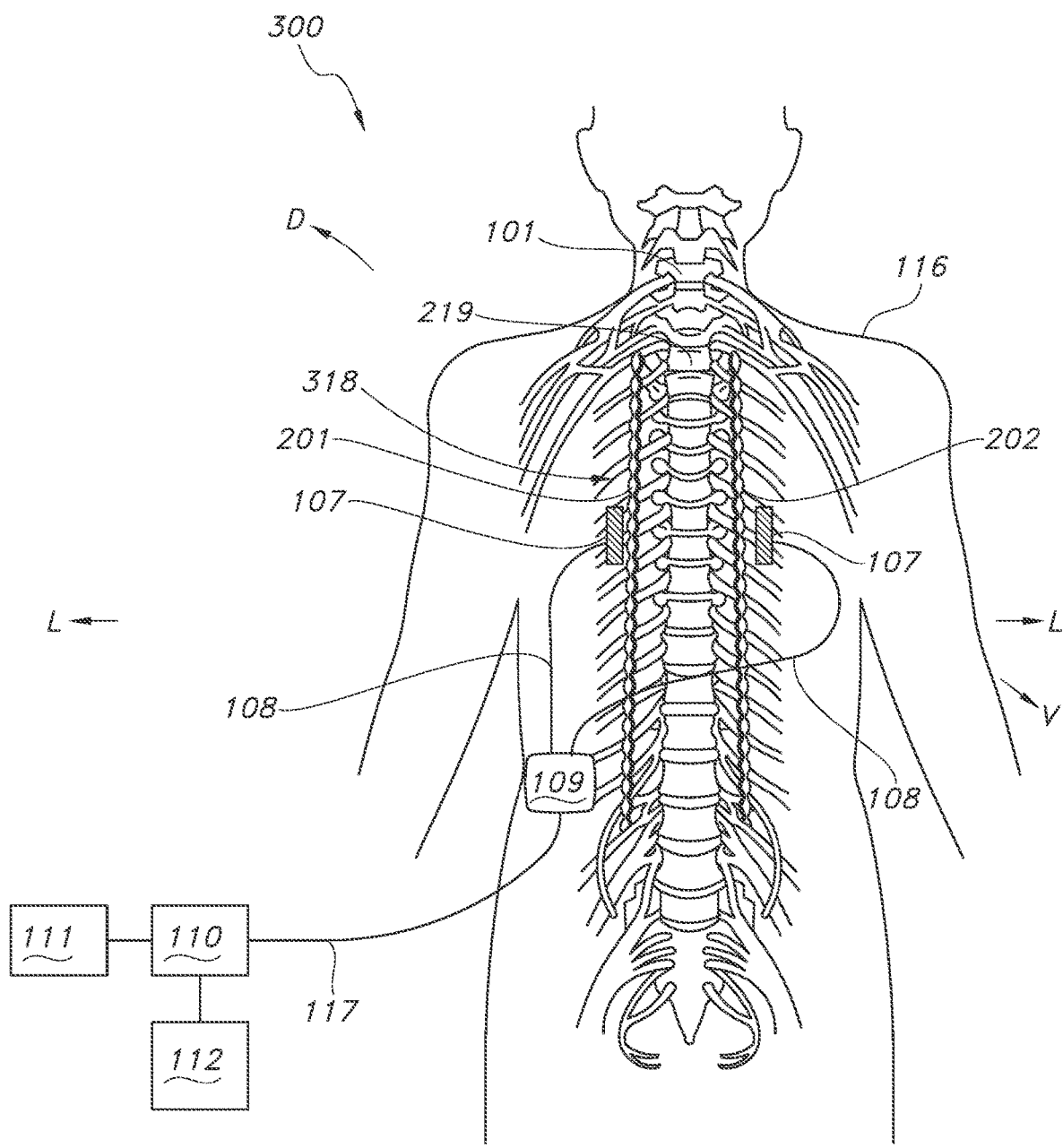
FIG. 8 illustrates at least one embodiment of a system for delivering one or more electrical signals to target neural tissue, non-neural tissue, or a combination thereof in a patient, where the target tissue is located within or adjacent a sympathetic chain ganglion.

Referring now to FIG. 8, there is illustrated a system 300 for delivering one or more electrical signals to provide therapy to a patient 116, where the target neural tissue, non-neural tissue, or a combination thereof 318 located adjacent a ventral or anterior region 219 of a spinal cord 101 of the patient 116. It should be appreciated that the system 300 of FIG. 8 may include similar elements and/or features to the system 50 described in reference to FIG. 1. In particular, the target neural tissue, non-neural tissue, or a combination thereof 318 can be a sympathetic chain ganglion located in the right sympathetic chain 201, the left sympathetic chain 202, or a combination thereof. As shown in FIG. 8, in some embodiments, the system 300 can include multiple devices to control and deliver electrical signals to an area within or adjacent target neural tissue, non-neural tissue, or a combination thereof 318 located adjacent a ventral V (or anterior) region 219 of the spinal cord 101 to provide therapy to the patient 116. In general, the system 300 of FIG. 8 can include one or more electrodes 107 that are connected by an electrical lead 108 to a signal generator 109. As described herein, multiple electrodes 107 may be arranged into an electrode array in some embodiments (see, e.g., FIGS. 11-18). An additional lead 117 can be used to couple the signal generator 109 to the rest of the system 300, which can include a user interface 112, and a controller 110, where it is to be understood that as an alternative to the use of the lead 117, the signal generator 109 can be wirelessly connected to the rest of the system 50. The system may also include an isolated power system 111 and/or a patient monitor system. Further, it should be understood that while the system 300 of FIG. 8 illustrates a configuration where electrical signals can be delivered to target neural tissue, non-neural tissue, or a combination thereof utilizing an electrode or electrodes 107 coupled to an implantable signal generator 109 via a lead 108, the electrode or electrodes 107 can alternatively be coupled to an external signal generator via a wireless antenna system. Regardless, the electrode or electrodes 107 can be in the form of an electrode assembly that can that can deliver electrical signals to a patient to provide therapy to the patient and/or improve one or more of the patient's symptoms.

Figure 9:
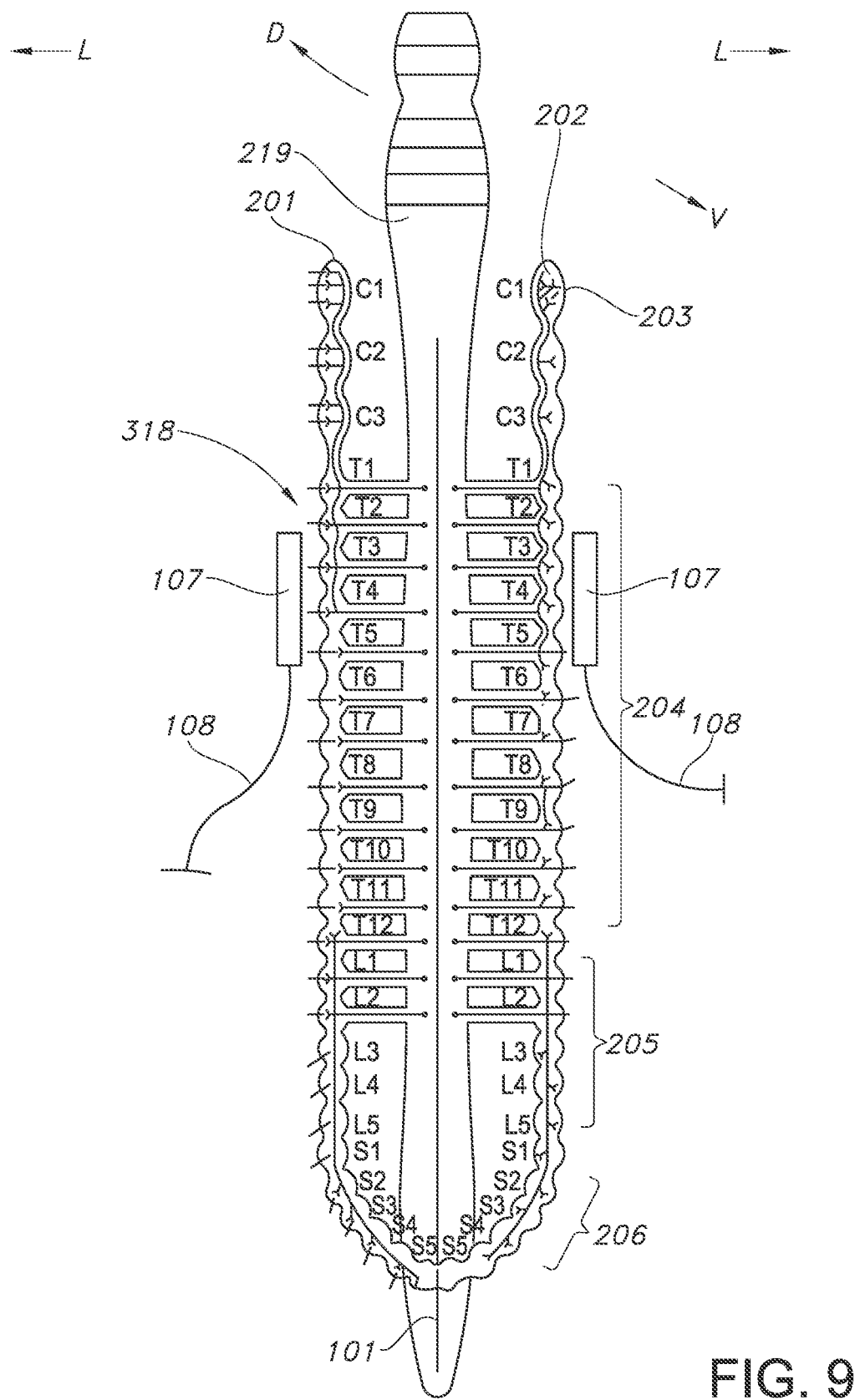
FIG. 9 is a zoomed-in view of the sympathetic chain and illustrates at least one option for electrode placement according to the system of FIG. 8.

Referring now to FIG. 9, the placement of the electrode or electrodes 107 (e.g., an electrode array) is discussed in more detail. For instance, one or more electrodes 107 can be positioned adjacent a region of the right sympathetic chain 201 or the left sympathetic chain 202 of the patient 116, where the sympathetic chains 201 and 202 are located ventral and lateral to a ventral (or anterior) region 219 of the spinal cord 101. By placing the electrode or electrodes 107 adjacent target neural tissue, non-neural tissue, or a combination thereof 318 located lateral and ventral to a ventral (or anterior) region 219 of the spinal cord 101, one or more electrical signals can be delivered to the target neural tissue, non-neural tissue, or a combination thereof 318 (e.g., a ganglion or ganglia of the right sympathetic chain 201 or the left sympathetic chain 202) to provide therapy to the patient.

For instance, electrical signals can be delivered to a ganglion or ganglia associated with the cervical portion 203, the thoracic portion 204, the lumbar portion 205, or the sacral portion 206 of the right sympathetic chain 201 or the left sympathetic chain 202, or any combination thereof to provide therapy to the targeted area or areas. In one particular embodiment, one or more electrodes 107 (e.g., an electrode array) can be placed adjacent the cervical region 203 of the sympathetic chain to affect nerve fiber activity associated with levels C1-C3, which can affect nerve fiber activity associated with the eyes, the lachrymal glands, the salivary glands, and the sweat glands, hair follicles, and blood vessels of the head, neck, and arms. In another embodiment, one or more electrodes 107 (e.g., an electrode array) can be placed adjacent levels T1-T4 of the thoracic region 204, which can affect nerve fiber activity associated with the heart and lungs. In an additional embodiment, one or more electrodes 107 (e.g., an electrode array) can be placed adjacent levels T5-T9 of the thoracic region 204, which can affect nerve fiber activity associated with the stomach, duodenum, pancreas, liver, kidneys, and adrenal medulla. In yet another embodiment, one or more electrodes 107 (e.g., an electrode array) can be placed adjacent levels T10-T11 of the thoracic region 204, which can affect nerve fiber activity associated with the stomach and duodenum. In one more embodiment, one or more electrodes 107 (e.g., an electrode array) can be placed adjacent level T12 of the thoracic region 204 and levels L1-L3 of the lumbar region 205, which can affect nerve fiber activity in the colon, rectum, bladder, and external genitalia. In still another embodiment, one or more electrodes 107 (e.g., an electrode array) can be placed adjacent levels L4-L5 of the lumbar region 205 and levels S1-S3 of the sacral region 206, which can affect nerve fiber activity associated with the sweat glands, hair follicles, and blood vessels of the lower limbs. In another embodiment, one or more electrodes 107 (e.g., an electrode array) can be placed adjacent levels S4-S5 of the sacral region 206, which can affect nerve fiber activity associated with the sweat glands, hair follicles, and blood vessels of the perineum. Specific diseases or conditions that can be treated based on stimulation of a sympathetic nervous system include, for example, complex regional pain syndrome, peripheral vascular disease and chronic limb ischemia, angina pain, diabetic pain, abdominal/visceral pain syndrome, phantom limb pain, Raynaud's syndrome, diabetic peripheral neuropathy, hypertension, hypotension, headache and migraine, and inflammatory pain such as arthritis, irritable bowel pain, osteoarthritis pain, and fibromyalgia. It should be appreciated that, in some embodiments, the electrode(s) 107 may be placed beside other autonomic structures including parasympathetic nerves (e.g., vagus nerve).

Figure 10:
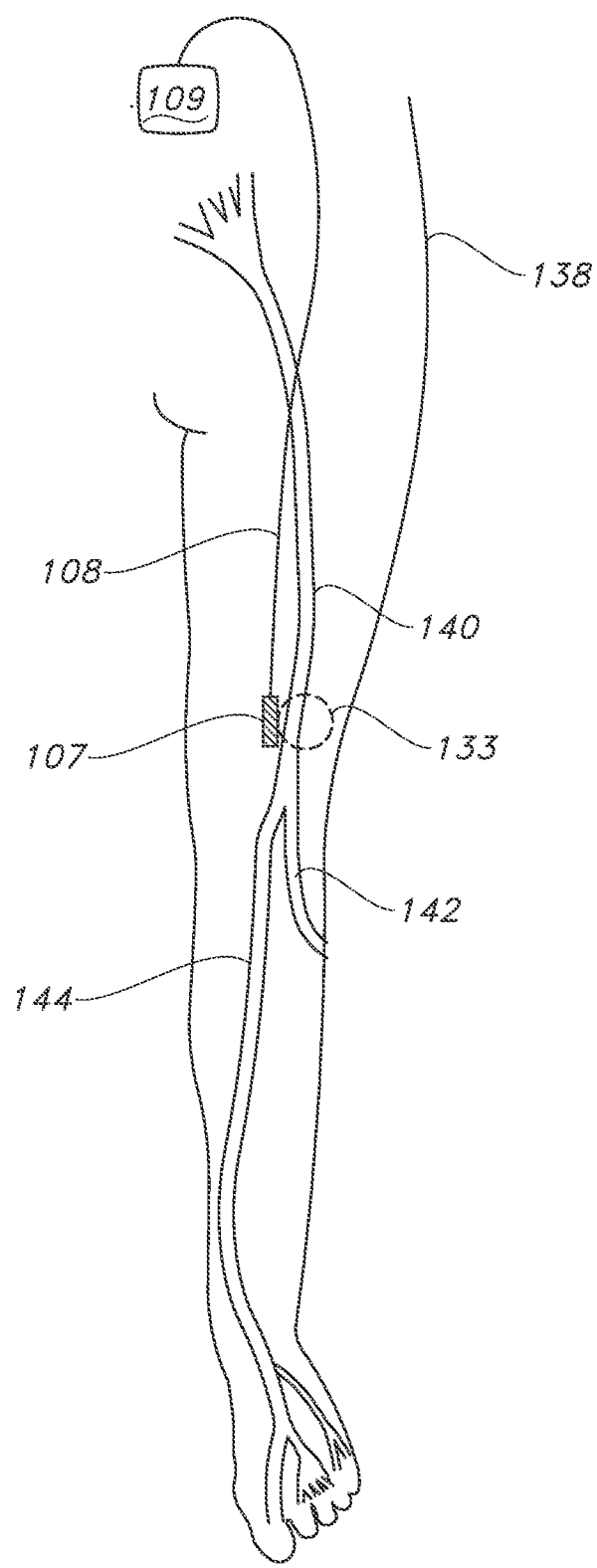
FIG. 10 illustrates at least one embodiment of a system for delivering one or more electrical signals to target neural tissue, non-neural tissue, or a combination thereof in a patient, where the target tissue is located within or adjacent a peripheral nerve.

Referring now to FIG. 10, the placement of the electrode or electrodes 107 (e.g., an electrode array) in order to deliver one or more electrical signals to an area within or adjacent target neural tissue, non-neural tissue, or a combination thereof 133 located adjacent or near a peripheral nerve is discussed in more detail. For instance, one or more electrodes 107 can be positioned near or adjacent a peripheral nerve at any location along its length, where the peripheral nerve can run, for instance, down the length of the leg 138 of the patient 116. In the particular embodiment of FIG. 10, the target tissue 133 is located adjacent the sciatic nerve 140, although it is to be understood that neural tissue, non-neural tissue, or a combination thereof can be located adjacent any peripheral nerve in the leg (e.g., the common peroneal nerve 142, the tibial nerve 144, etc.), or any other location in the body. By placing the electrode or electrodes 107 adjacent or near a peripheral nerve, electrical signals can be delivered to the target neural tissue, non-neural tissue, or a combination thereof 133 to provide therapy to the patient. Specific diseases or conditions that can be treated based on stimulation of a peripheral nerve include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, headache and migraine, cervical neuritis, post-herpetic neuralgia, vertigo, tinnitus, hearing loss and inflammatory pain such as arthritis, irritable bowel pain, overactive bladder, bowel incontinence or constipation, osteoarthritis pain, and fibromyalgia. For example, electrical signals can be used to stimulate the sacral nerve roots to treat overactive bladder, fecal incontinence, and/or sexual dysfunction. In some embodiments, the electrode(s) may be placed adjacent or near a cranial nerve.

It should be appreciated from the description that the electrode(s) 107 may be placed in particular location in order to treat a particular condition using the electrical stimulation technologies described herein. For example, in an embodiment, the electrode(s) 107 may be placed within an epidural space between T7 and T12 of a thoracic portion of the patient's spine to treat the patient for spinal lumbar pain. In another embodiment, the electrode(s) 107 may be placed within an epidural space between C2 and T1 of a cervical portion of the patient's spine to treat the patient for spinal cervical pain. In another embodiment, the electrode(s) 107 may be placed within an epidural space between C2 and T8 of the patient's spine to treat angina pain. In another embodiment, the electrode(s) 107 may be placed within an epidural space between C2 and T8 of the patient's spine to treat abdominal pain. In another embodiment, the electrode(s) 107 may be placed within an epidural space between T10 and L5 of the patient's spine to treat peripheral vascular disease. In another embodiment, the electrode(s) 107 may be placed within an epidural space between T7 and T12 in the thoracic spine to treat spinal lumbar pain disorders. In another embodiment, the electrode(s) 107 may be placed within an epidural space between C2 and T1 of a cervical portion of the patient's spine to treat the patient for upper limb ischemia. In another embodiment, the electrode(s) 107 may be placed at or within a dorsal root ganglion of the patient's spin to treat chronic or acute pain. In another embodiment, the electrode(s) 107 may be placed within a sacral portion of the patient's spine to treat urinary or fecal incontinence. In various embodiments, the electrode(s) 107 may be placed near or around the lumbar sympathetic plexus, the celiac sympathetic plexus, the hypogastric sympathetic plexus, or the stellate ganglion to treat chronic or acute pain of the limb, abdomen, pelvic area, or upper extremity, respectively. In another embodiment, the electrode(s) 107 may be placed near or around the patient's brain to treat movement disorders, Parkinson's, pain, psychiatric and/or seizure disorders. In another embodiment, the electrode(s) 107 may be placed near or around the patient's vagus nerve to treat seizure disorders, obesity, pain, or autonomic disorders. In another embodiment, the electrode(s) 107 may be placed near or around a peripheral nerve of the patient to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's somatic tissue, muscles, connective tissue, or non-neural tissue to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's visceral tissue or organs, and non-neural tissue to treat acute pain, chronic pain, fecal or urinary incontinence, seizure disorders, movement disorders, obesity, spasticity, and to modulate other unpleasant neurological conditions.

The various components of the systems 50, 100, and 300 described in FIGS. 1-10 may form the portion of an electrical stimulation system 400 as described below in more detail in reference to FIG. 11.

Figure 11:
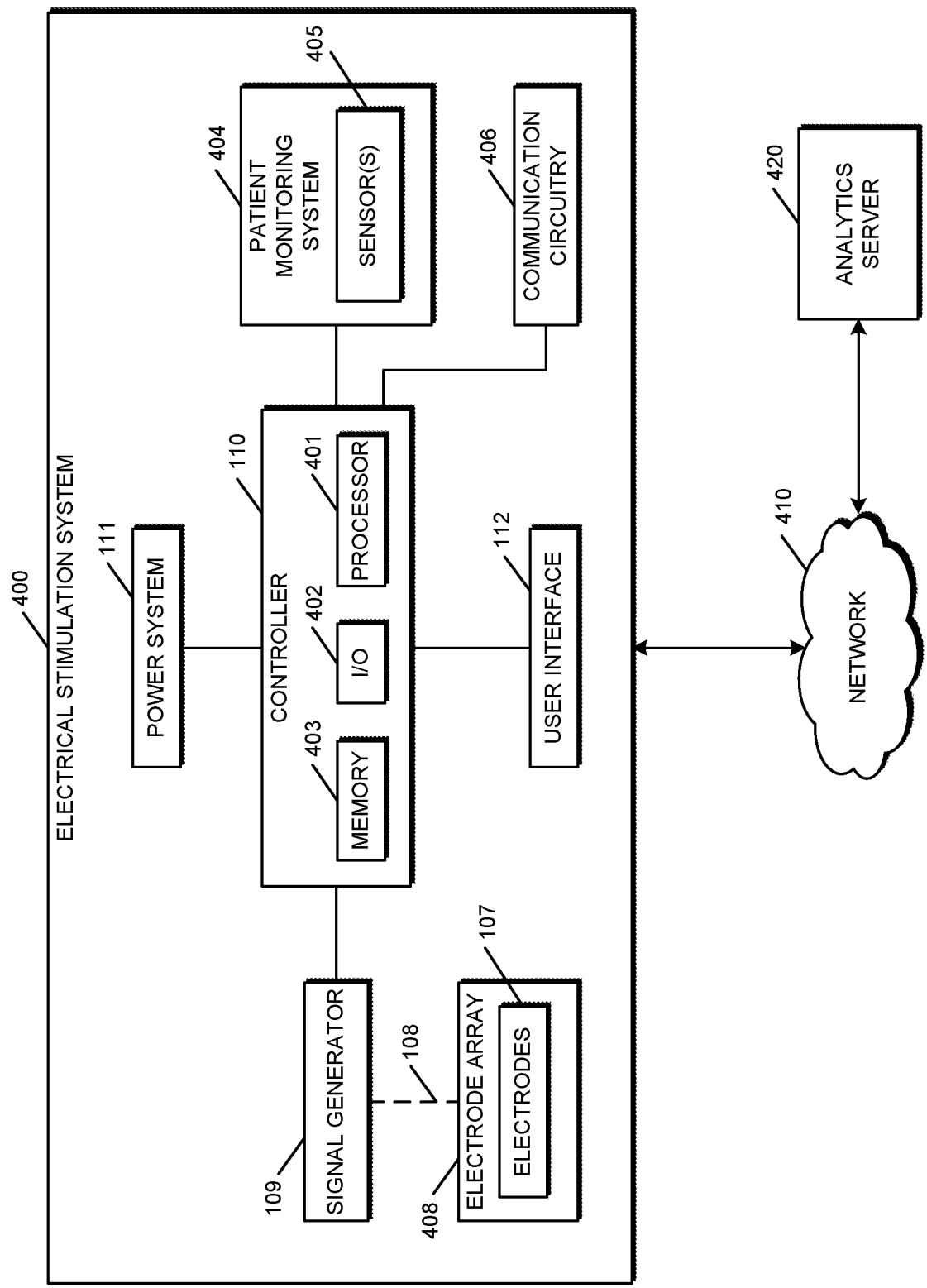
FIG. 11 is a simplified block diagram of at least one embodiment of an electrical stimulation system for providing therapy to a patient via the application of one or more electrical signals.

Referring now to FIG. 11, a simplified block diagram of at least one embodiment of an electrical stimulation system 400 for providing therapy to a patient via the application of one or more electrical signals and otherwise performing the functions described herein is shown. The illustrative electrical stimulation system 400 includes a plurality of electrodes 107, a signal generator 109, a controller 110, a power system 111, a user interface 112, a patient monitoring system 404, and a communication circuitry 406. Further, in the illustrative embodiment, the controller 110 includes a processor 401, an input/output ("I/O") subsystem 402, and a memory 403, and the patient monitoring system 404 includes one or more sensors 405. Additionally, as described herein, the electrodes 107 may collectively form one or more electrode arrays 408. It should be appreciated that one or more of the components of the electrical stimulation system 400 described herein may be embodied as, or form a portion of, one or more embedded controllers and/or integrated circuits. For example, in some embodiments, the processor 401, the I/O subsystem 402, the memory 403 and/or other components of the electrical stimulation system 400 may be embodied as, or form a portion of, a microcontroller or SoC (e.g., such as an embodiment in which the controller 110 is a microcontroller). Further, depending on the particular embodiment, the components of the electrical stimulation system 400 may be closely positioned to one another or spatially distributed (i.e., separated from one another) depending on the particular embodiment. Additionally, although only a single generator 109, controller 110, power system 111, user interface 112, patient monitoring system 404, communication circuitry 406, electrode array 408, processor 401, I/O subsystem 402, and memory 403 are illustratively shown in FIG. 11, it should be appreciated that a particular electrical stimulation system 400 may include multiple signal generators 109, controllers 110, power systems 111, user interfaces 112, patient monitoring systems 404, communication circuitries 406, electrode arrays 408, processors 401, I/O subsystems 402, and/or memories 403 in various embodiments. As described herein, it should be appreciated that the randomization of the stimulation can be managed by hardware, firmware, and/or software depending on the particular embodiment.

The electrodes 107 of the electrode array 408 can be used to deliver the electrical signals to the target neural tissue, non-neural tissue, or a combination thereof as described herein. Depending on the particular embodiment, the electrode array 408 can be implantable, percutaneous, or transcutaneous. Further, as described herein, the shape, size, material composition, inter-electrode spacing, and/or other parameters of the electrodes 107 or electrode array 408 can be specific to contouring the electrical field surrounding the target neural tissue, non-neural tissue, or a combination thereof, to enable specific therapy to be provided to the target neural tissue, non-neural tissue, or a combination thereof. It should be appreciated that the electrodes 107 of the electrode array 408 may be embodied on or electrically coupled to one or more electrical leads 108, which may be connected to the signal generator 109 as described herein. Various embodiments of the electrode array 408 are described in greater detail below in reference to FIGS. 13-20. It should be appreciated that the electrode array 408, the signal generator 109, and/or the controller 110 include electrical circuitry that allow for the real-time selection of specific electrodes 107 of the electrode array 408 as being electrical sources, electrical sinks, or unused/off during the transmission of an electrical stimulation signal.

In some embodiments, one or more of the electrodes 107 may contain a thermistor for recording tissue temperature during stimulation, and for providing feedback information for efficacy and safety measures, and temperature control. One or more of the electrodes 107 may also be configured to measure tissue impedance for providing feedback information for efficacy and safety measures, and impedance control. Lastly, a cooling mechanism may be incorporated into the electrode design to control temperature at the electrode-tissue interface. Independent current channels, electrolytic jelly, and electrode insulation may be used to prevent co-excitation of surrounding tissue and to optimize the electrical field that is exposed to the nerve. The electrode array 408 may be placed through a needle-like introducer assembly or applicator, and may include catheter-over-needle or needle-over-catheter approaches where the catheter may include electrical contacts for delivery of the stimulation waveform. The position of specific geometric features of the electrodes 107 and/or electrode array 408 (e.g. tip, side, different contacts, etc.) relative to the target structure may be optimized to provide the desired therapeutic effect with minimal undesired side-effects (such as co-excitation of nearby excitable tissues).

As shown in the figures, the electrodes 107 (or electrode array 408) may be connected to an implantable signal generator 109 through an electrical lead 108. Alternatively, in some embodiments, the signal generator 109 can be external and can be wirelessly connected to the electrodes 107 (or electrode array 408). In some embodiments, the signal generator 109 can be configured to generate and deliver electrical signals to provide therapy to a patient that can be customized based on patient feedback. As described herein, the patient feedback may be based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof.

The use of multiple signal generators 109 (or multiple waveform generators) may enhance the resolution of the signal generator 109 by independently powering some electrical contacts with one signal, and powering other contacts with a different signal, and/or by allowing one waveform to be added to another waveform and delivered through the same set of contacts. Accordingly, an electrical stimulation system 400 that contains multiple independent signal generators 109 (or multiple waveform generators) may enable improved control of electrical contacts, may enable improved control of the waveform's randomness, and/or may facilitate interactions between frequency bands (e.g., multi-waveform, physiological, and psychophysical masking).

Regardless of the particular type or combination of electrical signals utilized, the electrical signals can be adjusted, such that the energy contained within a particular frequency band, and for all frequency bands of energy delivered to the tissue, can be adjusted to best treat the patient as described herein. In illustrative embodiments, the adjustable electrical energy can be adjusted to deliver electrical signals with intensities ranging from about 1 mA (or 0.1 mA) to about 100 mA and from about 1 V (or 0.1 V) to about 200 V (peak-to-peak) for each frequency band included in the spectrum. In some embodiments, the spectrum of electrical signals includes frequencies ranging from about 0 Hz to about 100 kHz (or about 0 Hz to about 500 kHz), and is composed of adjustable frequency bands. It should be appreciated that the size of the frequency bands may vary depending on the particular embodiment (e.g., 10 Hz bands, 100 Hz bands, 1000 Hz bands, etc.). In some embodiments, the spectrum of electrical signals includes frequencies ranging from about 0 Hz to about 25 kHz (or about 0 Hz to about 25 kHz), and each of the frequency bands within the frequency range may have a bandwidth of 1 kHz or 2 kHz. In another embodiment, the electrical stimulation signal may have a frequency range of about 0.05 Hz to about 2 kHz, and/or each of the frequency bands within the frequency range may have a bandwidth of about 150 Hz. Although various frequency ranges are described herein as being "from about 0 Hz," it should be appreciated that such lower bound may be some non-zero frequency greater than 0 Hz in some embodiments (e.g., 1 Hz). Moreover, the frequency band that receives power can be determined in a random fashion.

The power supply, power source, or power system 111 is configured to supply power to the controller 110 and/or other components of the electrical stimulation system 400. In some embodiments, the power system 111 is an independent, untethered, and portable power source configured to supply power to the electrical stimulation system 400 to perform the various functions described herein. For example, the power system 111 may include one or more batteries, battery packs, capacitors, super capacitors, solar cells, and/or other power supplies. Depending on the particular embodiment, the power system 111 may or may not be rechargeable. In other embodiments, the power system 111 may be line powered via AC mains and/or another suitable power source. It should be appreciated that the power system 111 can include both external and internal portions, where the internal portion of the power system can include a battery, such as a lithium battery, and the external portion of the power system 111 can be plugged into a wall and used to recharge the battery as needed. In such embodiments, the external portion of the power system 111 can transmit power to the signal generator 109 as directed by the controller 110 via RF signals/electromagnetic induction, or power can be transmitted to the signal generator 109 via the battery in the internal portion of the power system 111. Further, the external portion of the power system 111 can be used to recharge the battery in the internal portion of the power system 111.

The user interface 112 may be embodied as any one or more devices or components that allow a user to interact with the electrical stimulation system 400. For example, in some embodiments, the user interface 112 can be in the form of a computer that interacts with the controller 110 and is powered by a power system 111. In particular, in some embodiments, the computer can operate software designed to record signals passed from the controller 110, and to drive the controller's output. Possible software packages include Cambridge Electronic Design's (UK) SPIKE program. The software can be programmable and can record and analyze electrophysiological signals, as well as direct the controller 110 to deliver the electrical signals described herein. Further, in some embodiments, the user interface 112 may include one or more peripheral devices such as, for example, a keyboard, mouse, display, status indicator, diagnostic tool, speaker, microphone, and/or one or more other suitable peripheral devices.

In some embodiments, the electrical stimulation system 400 may include a patient monitoring system 404. In such embodiments, the patient monitoring system 404 can acquire, amplify/attenuate, and filter physiological signals and then output them to the controller 110. It should be appreciated that the patient monitoring system 404 may include one or more sensors 405. The sensors 405 are configured to generate sensor data (e.g., by virtue of one or more signals), which may be interpreted by the controller 110 (e.g., the processor 401) to determine one or more characteristics associated with the patient and/or the electrical stimulation system 400. By way of example, the sensors 405 may detect various characteristics of the physical environment of the electrical stimulation system 400 (internal and/or external) and/or other suitable characteristics. In various embodiments, the sensors 405 may be embodied as, or otherwise include, environmental sensors, inertial sensors, proximity sensors, optical sensors, electromagnetic sensors, audio sensors, pressure sensors, flow meters, temperature sensors, thermistors, chemical sensors, biopotential electrodes, motion sensors, piezoelectric sensors, cameras, and/or other types of sensors. Of course, the electrical stimulation system 400 may also include components and/or devices configured to facilitate the use of the sensors 405. For example, in some embodiments, the patient monitoring system 404 may include a heart-rate monitor to collect electrocardiogram signals and/or a muscle activity monitor to collect electromyography signals. The heart-rate monitor can include ECG electrodes coupled with an alternating current (AC) amplifier, and the muscle activity monitor can include EMG electrodes coupled with an AC amplifier. Other types of transducers may also be used in other embodiments. As described, physiological signals obtained with the patient monitoring system 404 may be passed through an AC signal amplifier/conditioner. One possible amplifier/conditioner is a Model LP511 AC amplifier available from Grass Technologies, a subsidiary of Astro-Med, Inc., West Warwick, Rhode Island, USA.

The communication circuitry 406 may be embodied as any communication circuitry, transceiver, device, or collection thereof, capable of enabling communications between the electrical stimulation system 400 and other remote devices. The communication circuitry 406 may be configured to use any one or more wired and/or wireless communication technologies and associated protocols. For example, in some embodiments, the illustrative electrical stimulation system 400 may be configured to communicate via Wi-Fi (e.g., infrastructure or ad hoc mode), Wi-Fi Direct, Bluetooth (including Bluetooth Low Energy (BLE)), Zig-Bee, Z-wave, Near Field Communication (NFC), IEEE 802.15, HL7, and/or other suitable wireless communication protocol(s). Further, in some embodiments, the electrical stimulation system 400 may be configured to communicate via Ethernet, Power over Ethernet (PoE), serial communication links, power line communication, and/or another suitable wired communication mechanism.

The controller 110 may be embodied as any type of controller or control system capable of performing the functions described herein. In the illustrative embodiment, the controller 110 can record electrical signal data as well as digital information from the patient monitoring system 404, and can generate electrical signal and digital outputs simultaneously for real-time control of the signal generator 109 based on feedback received from the patient after transmission of the electrical stimulation signals. The controller 110 may have onboard memory to facilitate high-speed data capture, independent waveform sample rates, and on-line analysis. An exemplary controller 110 may be a POWER 1401 data-acquisition interface unit available from Cambridge Electronic Design (UK).

As shown, in some embodiments, the controller 110 includes a processor 401, an I/O subsystem 402, and memory 403.

The processor 401 may be embodied as any type of processor(s) capable of performing the functions described herein. In particular, the processor 401 may be embodied as one or more single or multi-core processors, microcontrollers, or other processor or processing/controlling circuits. For example, in some embodiments, the processor 401 may include or be embodied as an arithmetic logic unit (ALU), central processing unit (CPU), digital signal processor (DSP), and/or another suitable processor(s). The processor 401 may be a programmable type, a dedicated hardwired state machine, or a combination thereof. One or more processors 401 with multiple processing units may utilize distributed, pipelined, and/or parallel processing in various embodiments. Further, the processor 401 may be dedicated to performance of just the operations described herein, or may be utilized in one or more additional applications. In the illustrative embodiment, the processor 401 is of a programmable variety that executes algorithms and/or processes data in accordance with operating logic as defined by programming instructions (such as software or firmware) stored in the memory 403. Additionally or alternatively, the operating logic for the processor 401 may be at least partially defined by hardwired logic or other hardware. Further, the processor 401 may include one or more components of any type suitable to process the signals received from input/output devices or from other components or devices and to provide desired output signals. Such components may include digital circuitry, analog circuitry, or a combination thereof.

The memory 403 may be of one or more types of non-transitory computer-readable media, such as a solid-state memory, electromagnetic memory, optical memory, or a combination thereof. Furthermore, the memory 403 may be volatile and/or nonvolatile and, in some embodiments, some or all of the memory 403 may be of a portable variety, such as a disk, tape, memory stick, cartridge, and/or other suitable portable memory. In operation, the memory 403 may store various data and software used during operation of the electrical stimulation system 400 such as operating systems (e.g., real-time operating systems (RTOS)), applications, programs, libraries, and drivers. The memory 403 is communicatively coupled to the processor 401 via the I/O subsystem 402, which may be embodied as circuitry and/or components to facilitate input/output operations with the processor 401, the memory 403, and other components of the electrical stimulation system 400. For example, the I/O subsystem 402 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. Depending on the particular embodiment, the memory 403 may be included with the processor 401 and/or coupled to the processor 401 depending on the particular embodiment. For example, in some embodiments, the processor 401, the I/O subsystem 402, the memory 403, and/or other components of the electrical stimulation system 400 may form a portion of a system-on-a-chip (SoC) and be incorporated on a single integrated circuit chip.

As shown in FIG. 11, in some embodiments, the electrical stimulation system 400 or a portion thereof (e.g., the controller 110) may be configured to communicate with an analytics server 420 and/or other remote computing device via a network 410. For example, in some embodiments, the electrical stimulation system 400 may transmit patient data (e.g., including an optimal electrical stimulation signature), sensor data, and/or other data to the analytics server 420 for leveraging artificial intelligence, machine learning, and/or other technologies for pattern identification and/or decision-making.

The network 410 may be embodied as any type of communication network capable of facilitating communication between the electrical stimulation system 400 and the analytics server 420 and/or other remote devices. As such, the network 410 may include one or more networks, routers, switches, computers, and/or other intervening devices. For example, the network 410 may be embodied as or otherwise include one or more cellular networks, telephone networks, local or wide area networks, publicly available global networks (e.g., the Internet), ad hoc networks, short-range communication links, or a combination thereof.

The analytics server 420 may be embodied as any type of device(s) capable of performing the functions described herein. It should be appreciated that the efficacy of neuromodulation technologies is affected by continuously changing treatment variables. Treatment variables may be device-specific (e.g., lead migration and impedance changes, stimulation paradigm, etc.), physiological (e.g., neurological conditioning or tolerance, scar tissue formation, plasticity, etc.), psychological (e.g., depression, etc.), disease state specific (e.g., progression, improvement, etc.) and/or patient dependent (e.g., height, weight, age, race, etc.). Moreover, these treatment variables generally change with time and may interact (stim* time interaction, long-term physiological changes, etc.).

In some embodiments, the inputs for a neural network or other machine learning algorithm used by the analytics server 420 may include one or more of adjusted electrical stimulation signatures, patient information, patient demographics, diagnosis information, electrode positioning, patient sensations, measures of treatment efficacy and/or outcomes (e.g., Pain Rating Scale scores), time of day, duration of treatment, time elapsed since start of treatment plan, and/or other machine learning model inputs. Further, in various embodiments, the analytics server 420 may utilize any machine learning and/or artificial intelligence algorithm for performing the functions described herein. For example, in some embodiments, the analytics server 420 may utilize one or more neural network algorithms, regression algorithms, instance-based algorithms, regularization algorithms, decision tree algorithms, Bayesian algorithms, clustering algorithms, association rule learning algorithms, deep learning algorithms, dimensionality reduction algorithms, and/or other suitable machine learning algorithms, techniques, and/or mechanisms.

It should be further appreciated that, although the analytics server 420 is described herein as a computing device outside of a cloud computing environment, in other embodiments, the analytics server 420 may be embodied as a cloud-based device or collection of devices within a cloud computing environment. Further, in cloud-based embodiments, the analytics server 420 may be embodied as a server-ambiguous computing solution, for example, that executes a plurality of instructions on-demand, contains logic to execute instructions only when prompted by a particular activity/trigger, and does not consume computing resources when not in use. That is, the analytics server 420 may be embodied as a virtual computing environment residing "on" a computing system (e.g., a distributed network of devices) in which various virtual functions (e.g., Lambda functions, Azure functions, Google cloud functions, and/or other suitable virtual functions) may be executed corresponding with the functions of the analytics server 420 described herein. For example, when an event occurs (e.g., data is transferred to the analytics server 420 for handling), the virtual computing environment may be communicated with (e.g., via a request to an API of the virtual computing environment), whereby the API may route the request to the correct virtual function (e.g., a particular server-ambiguous computing resource) based on a set of rules. For example, when a request for the transmission of data is made (e.g., via an appropriate user interface to the analytics server 420), the appropriate virtual function(s) may be executed to perform the actions before eliminating the instance of the virtual function(s).

Figure 12:
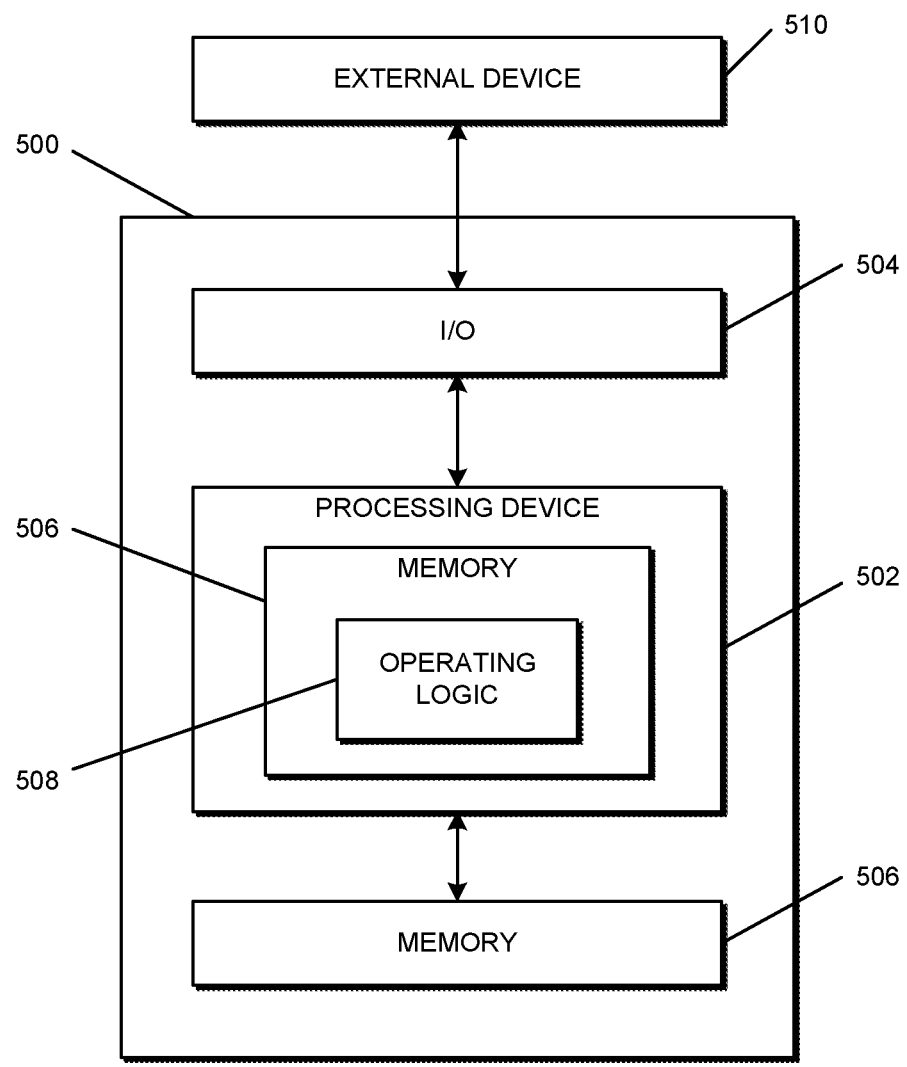
FIG. 12 is a simplified block diagram of at least one embodiment of a computing system.

Referring now to FIG. 12, a simplified block diagram of at least one embodiment of a computing device 500 is shown. The illustrative computing device 500 depicts at least one embodiment of a server that may be utilized in connection with the analytics server 420 illustrated in FIG. 12 and/or other devices in communication with the electrical stimulation system 400. Depending on the particular embodiment, the computing device 500 may be embodied as a server, desktop computer, laptop computer, tablet computer, notebook, netbook, Ultrabook™, mobile computing device, cellular phone, smartphone, wearable computing device, personal digital assistant, Internet of Things (IoT) device, processing system, router, gateway, and/or any other computing, processing, and/or communication device capable of performing the functions described herein.

The computing device 500 includes a processing device 502 that executes algorithms and/or processes data in accordance with operating logic 508, an input/output device 504 that enables communication between the computing device 500 and one or more external devices 510, and memory 506 which stores, for example, data received from the external device 510 via the input/output device 504.

The input/output device 504 allows the computing device 500 to communicate with the external device 510. For example, the input/output device 504 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 500 may be configured to use any one or more communication technologies (e.g., wireless or wired communications) and associated protocols (e.g., Ethernet, Bluetooth®, Wi-Fi®, WiMAX, etc.) to effect such communication depending on the particular computing device 500. The input/output device 504 may include hardware, software, and/or firmware suitable for performing the techniques described herein.

The external device 510 may be any type of device that allows data to be inputted or outputted from the computing device 500. For example, in various embodiments, the external device 510 may be embodied as the analytics server 420 and/or the electrical stimulation system 400. Further, in some embodiments, the external device 510 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 510 may be integrated into the computing device 500.

The processing device 502 may be embodied as any type of processor(s) capable of performing the functions described herein. In particular, the processing device 502 may be embodied as one or more single or multi-core processors, microcontrollers, or other processor or processing/controlling circuits. For example, in some embodiments, the processing device 502 may include or be embodied as an arithmetic logic unit (ALU), central processing unit (CPU), digital signal processor (DSP), and/or another suitable processor(s). The processing device 502 may be a programmable type, a dedicated hardwired state machine, or a combination thereof. Processing devices 502 with multiple processing units may utilize distributed, pipelined, and/or parallel processing in various embodiments. Further, the processing device 502 may be dedicated to performance of just the operations described herein, or may be utilized in one or more additional applications. In the illustrative embodiment, the processing device 502 is programmable and executes algorithms and/or processes data in accordance with operating logic 508 as defined by programming instructions (such as software or firmware) stored in memory 506. Additionally or alternatively, the operating logic 508 for processing device 502 may be at least partially defined by hardwired logic or other hardware. Further, the processing device 502 may include one or more components of any type suitable to process the signals received from input/output device 504 or from other components or devices and to provide desired output signals. Such components may include digital circuitry, analog circuitry, or a combination thereof.

The memory 506 may be of one or more types of non-transitory computer-readable media, such as a solid-state memory, electromagnetic memory, optical memory, or a combination thereof. Furthermore, the memory 506 may be volatile and/or nonvolatile and, in some embodiments, some or all of the memory 506 may be of a portable type, such as a disk, tape, memory stick, cartridge, and/or other suitable portable memory. In operation, the memory 506 may store various data and software used during operation of the computing device 500 such as operating systems, applications, programs, libraries, and drivers. It should be appreciated that the memory 506 may store data that is manipulated by the operating logic 508 of processing device 502, such as, for example, data representative of signals received from and/or sent to the input/output device 504 in addition to or in lieu of storing programming instructions defining operating logic 508. As shown in FIG. 12, the memory 506 may be included with the processing device 502 and/or coupled to the processing device 502 depending on the particular embodiment. For example, in some embodiments, the processing device 502, the memory 506, and/or other components of the computing device 500 may form a portion of a system-on-a-chip (SoC) and be incorporated on a single integrated circuit chip.

In some embodiments, various components of the computing device 500 (e.g., the processing device 502 and the memory 506) may be communicatively coupled via an input/output subsystem, which may be embodied as circuitry and/or components to facilitate input/output operations with the processing device 502, the memory 506, and other components of the computing device 500. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 500 may include other or additional components, such as those commonly found in a typical computing device (e.g., various input/output devices and/or other components), in other embodiments. It should be further appreciated that one or more of the components of the computing device 500 described herein may be distributed across multiple computing devices. In other words, the techniques described herein may be employed by a computing system that includes one or more computing devices. Additionally, although only a single processing device 502, I/O device 504, and memory 506 are illustratively shown in FIG. 12, it should be appreciated that a particular computing device 500 may include multiple processing devices 502, I/O devices 504, and/or memories 506 in other embodiments. Further, in some embodiments, more than one external device 510 may be in communication with the computing device 500.

As described above, the electrical stimulation system 400 is configured to randomly deliver electrical stimuli through a set of electrodes in an electrode array 408 to neural and/or non-neural tissue, in order to more effectively treat acute/chronic pain and/or other medical conditions while avoiding neurological tolerance in the patient. More specifically, in various illustrative embodiments, the electrical stimulation system 400 utilizes an electrode array 408 including a plurality of electrodes 107 (e.g., three or more) that delivers spatially random electrical stimulation to the patient. Various embodiments of the electrode array 408 and corresponding electrical configurations are depicted and described in reference to FIGS. 13-20.

Figure 13:
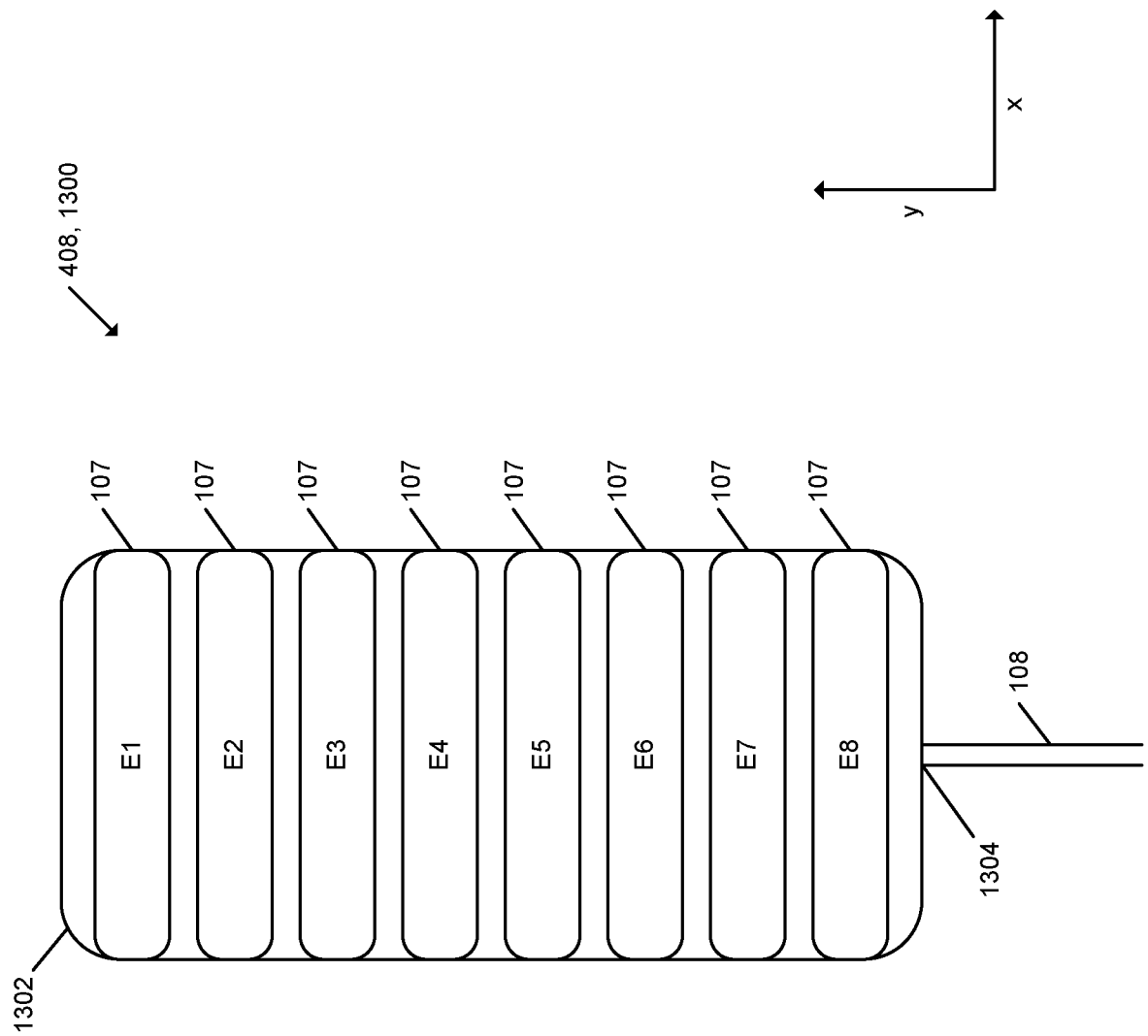
FIG. 13 illustrates at least one embodiment of an electrode array of an electrical stimulation device.

Referring now to FIG. 13, at least one embodiment of an electrode array 1300 is shown as part of an electrode assembly 1302. As shown, the illustrative electrode array 1300 includes eight electrodes 107, which are labeled as E1-E8 for convenience. Although the illustrative embodiment of the electrode array 1300 depicts eight electrodes 107, it should be appreciated that the electrode array 1300 may include a greater or lesser number of electrodes in other embodiments. It should be appreciated that the electrode array 1300 (or, more specifically, the electrodes 107 thereof) may be electrically coupled to a signal generator 109 through a lead 108 as described herein. As shown, in the illustrative embodiment, the electrode assembly 1302 is relatively rectangular in cross-sectional shape, extending lengthwise and distally from a point of connection 1304 with the lead 108 (e.g., along a y-axis). However, it should be appreciated that the electrode assembly 1302 may be otherwise shaped in other embodiments (e.g., cylindrical). In the illustrative embodiment, each of the electrodes 107 (i.e., E1-E8) extends laterally across the electrode assembly 1302 (e.g., along an x-axis) and is spatially separated from the other electrodes 107 (e.g., to avoid electrical interference between electrodes 107 and/or other unwanted electrical/electromagnetic characteristics). In the illustrative embodiment, the E1 electrode 107 is depicted as the most distal electrode 107, and the E8 electrode 108 is depicted as the most proximal electrode 107. In other embodiments, however, it should be appreciated that the lead 108 may otherwise connect with the electrode assembly 1302.

In use, in the illustrative embodiment, the controller 110 of the electrical stimulation system 400 is configured to randomly select a set of one or more electrodes 107 (e.g., from E1-E8) to function as electrical sources and a separate set of one or more electrodes 107 (e.g., from E1-E8) to function as electrical sinks. It should be appreciated that the remaining electrodes 107 (e.g., from E1-E8) that have not been selected to function as electrical sources or electrical sinks may remain off or otherwise non-functioning. Further, in some embodiments, the number of electrodes 107 selected as sources and/or the number of electrodes 107 selected as sinks may also be randomly determined. In some embodiments, the controller 110 may also randomly select the polarity of the assignment. It should be appreciated that the electrical stimulation system 400 may use any suitable combination of hardware, firmware, and/or software and/or any suitable algorithm or technique to perform the random selections described herein.

Figure 14:
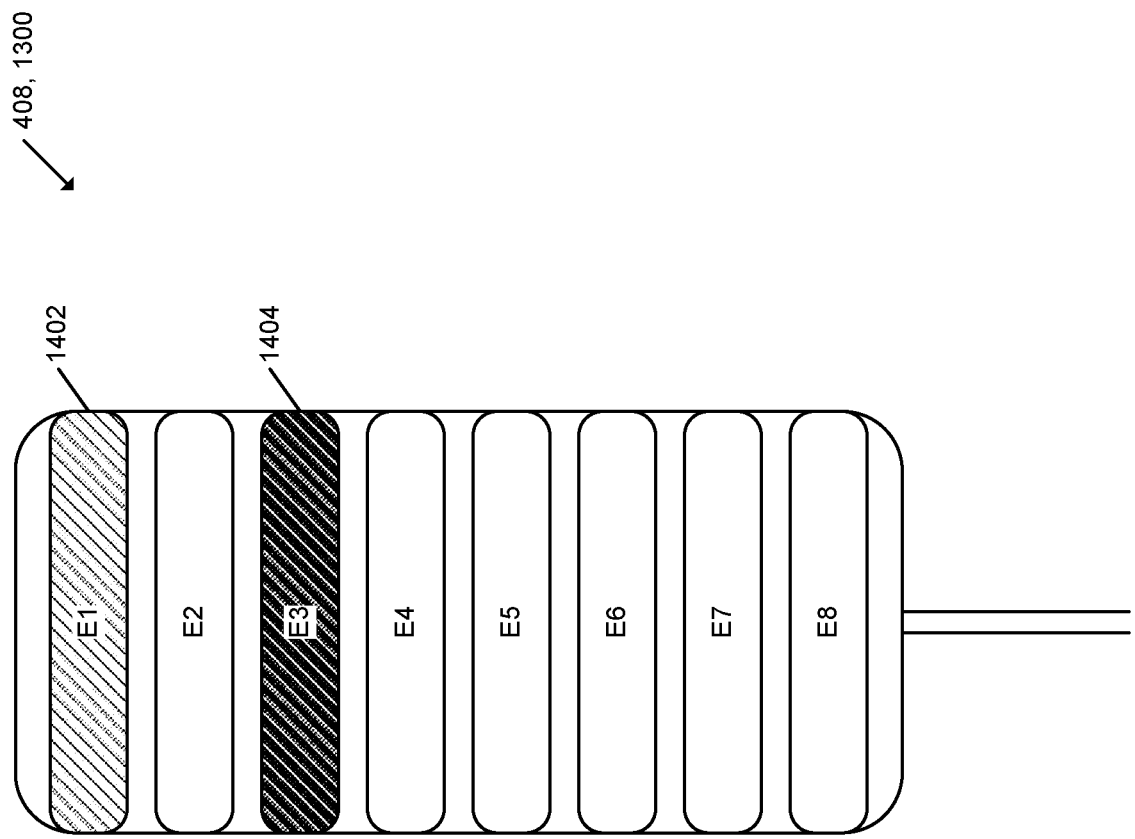
FIGS. 14-17 illustrates various electrical configurations of the electrode array of FIG. 13.
Figure 15:
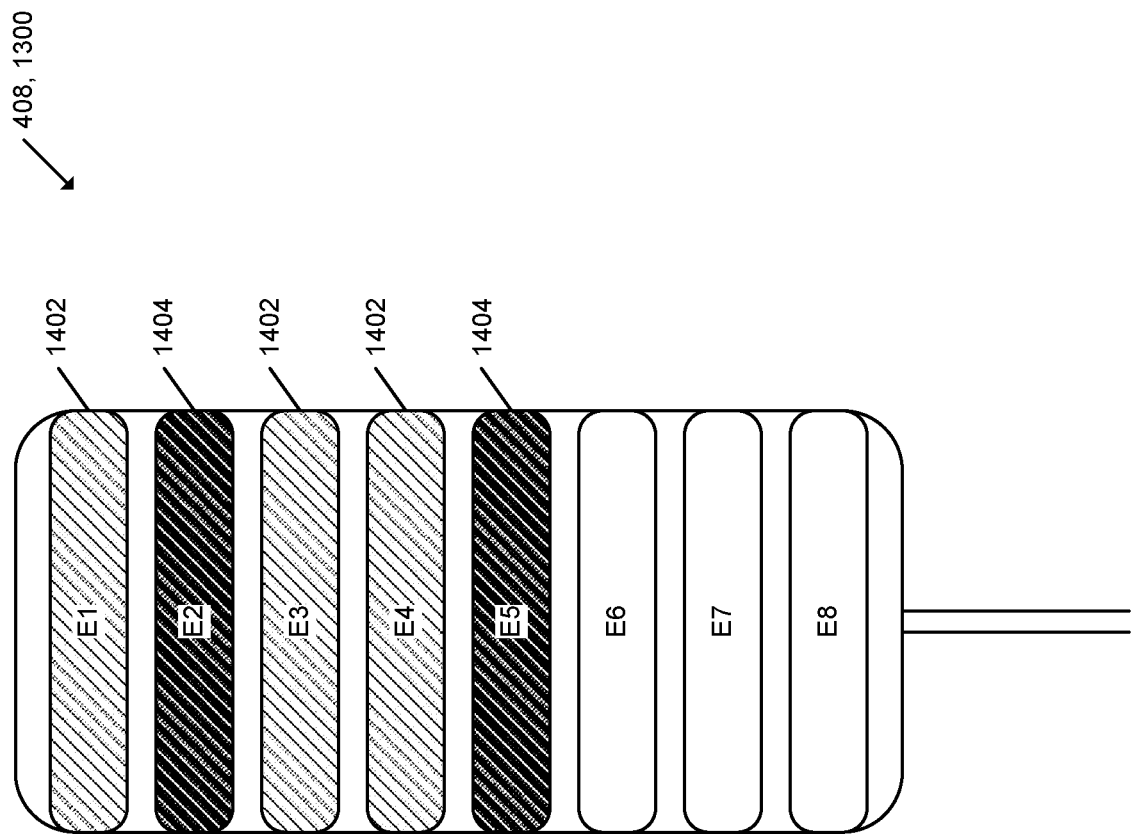
Figure 16:
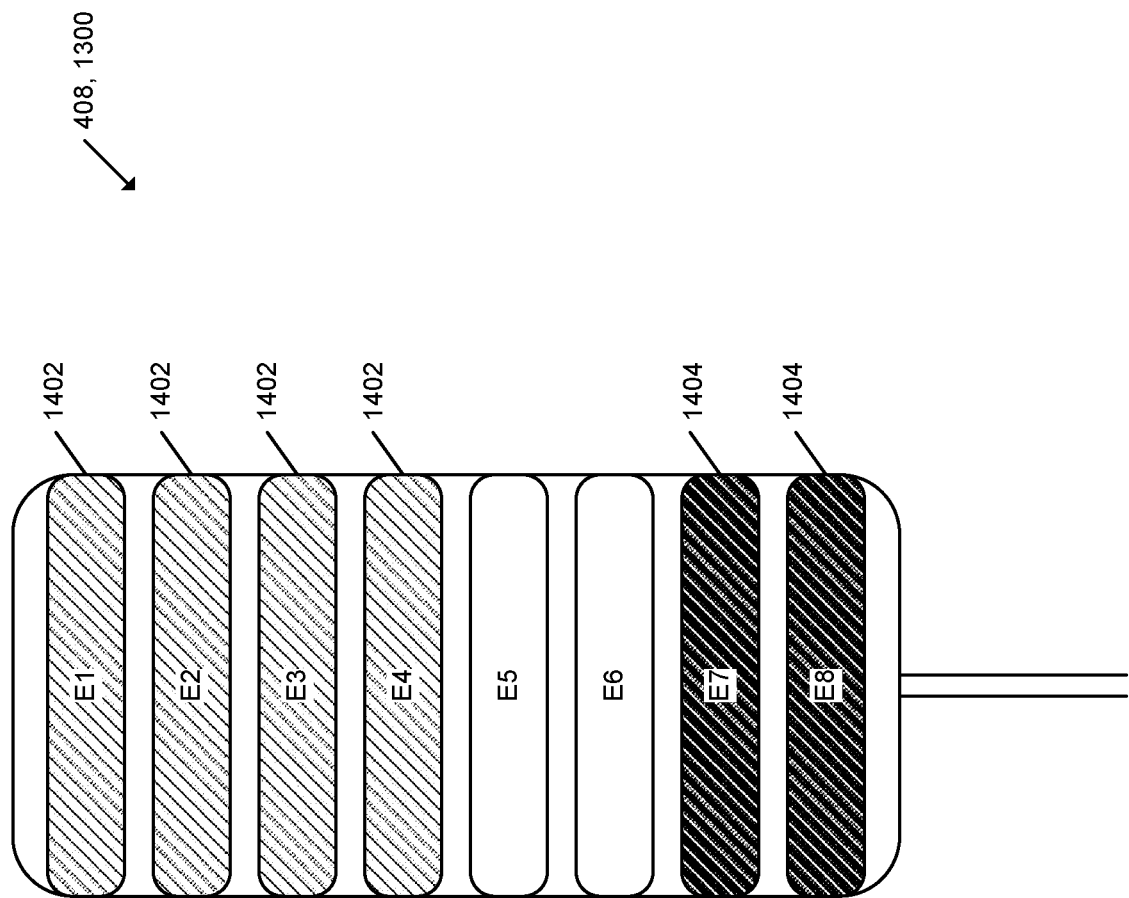
Figure 17:
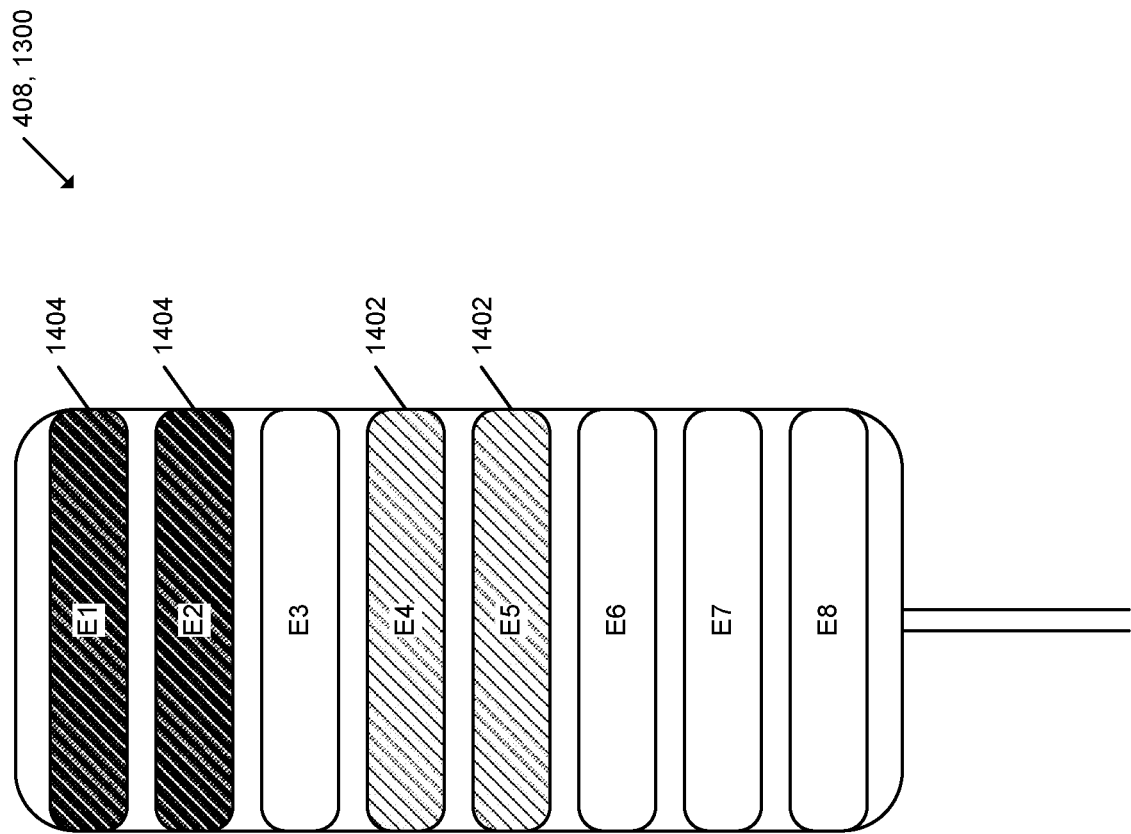

By way of example, FIGS. 14-17 illustrate various electrical configurations of the electrode array 1300 that could be randomly selected by the controller 110. FIG. 14 depicts a configuration in which the controller 110 has randomly selected the E1 electrode 107 to be a source 1402 and the E3 electrode 107 to be a sink 1404. FIG. 15 depicts a configuration in which the controller 110 has randomly selected the E1, E3, and E4 electrodes 107 to be sources 1402 and the E2 and E5 electrodes 107 to be sinks 1404. FIG. 16 depicts a configuration in which the controller 110 has randomly selected the E1, E2, E3, and E4 electrodes 107 to be sources 1402 and the E7 and E8 electrodes 107 to be sinks 1404. FIG. 17 depicts a configuration in which the controller 110 has randomly selected the E4 and E5 electrodes 107 to be sources 1402 and the E1 and E2 electrodes to be sinks 1404.

It should be appreciated that the amount of time that a particular signal is delivered to the patient through the selected electrical configuration of source electrode(s) 107 and sink electrode(s) 107 may vary depending on the particular embodiment. For example, in some embodiments, the controller 110 may instruct the signal generator 109 to deliver the signal through the selected electrical configuration of source electrode(s) 107 and sink electrode(s) 107 for a threshold period of time, after which the controller 110 again randomly selects a new electrical configuration of source electrode(s) 107 and sink electrode(s) 107 and instructs the signal generator 109 to deliver the same signal (or different signal) through the newly selected electrical configuration of source electrode(s) 107 and sink electrode (s) 107 for the threshold period of time. Further, it should be appreciated that the controller 110 may utilize any suitable technique for measuring time and determining the threshold period of time (e.g., number of clock cycles, number of pulses for a pulse-based signal, number of periods for a periodic signal, portions thereof, etc.). For example, in an embodiment, the controller 110 may instruct the signal generator 109 to deliver a set of pulses to the patient in which a first pulse is delivered through the electrode array 1300 using the electrical configuration of FIG. 15, a second pulse is delivered through the electrode array 1300 using the electrical configuration of FIG. 16, and a third pulse is delivered through the electrode array 1300 using the electrical configuration of FIG. 17. Further, in some embodiments, the controller 110 may utilize sensed data and/or feedback to determine the amount of time that a particular signal is delivered to the patient through the selected electrical configuration of source electrode(s) 107 and sink electrode(s) 107. For example, the relevant threshold may be based on the amount of charge injected by the electrode(s) 107, charge per pulse, charge density, feedback from the controller 110 (e.g., based on previous stimulation history), and/or other characteristics.

As described herein, in various embodiments, the electrical stimulation signal may be a periodic signal, aperiodic signal, impulses, pulses, direct current waveform, noise signal, and/or another waveform (e.g., 0-1 MHz). Further, in some embodiments, the electrical stimulation signal has been tuned (or is being tuned) to treat the patient by adjusting various characteristics of the signal (e.g., adjusting the amplitude of the voltage/current, power, and/or phase of the signal within various frequency bands).

Figure 18:
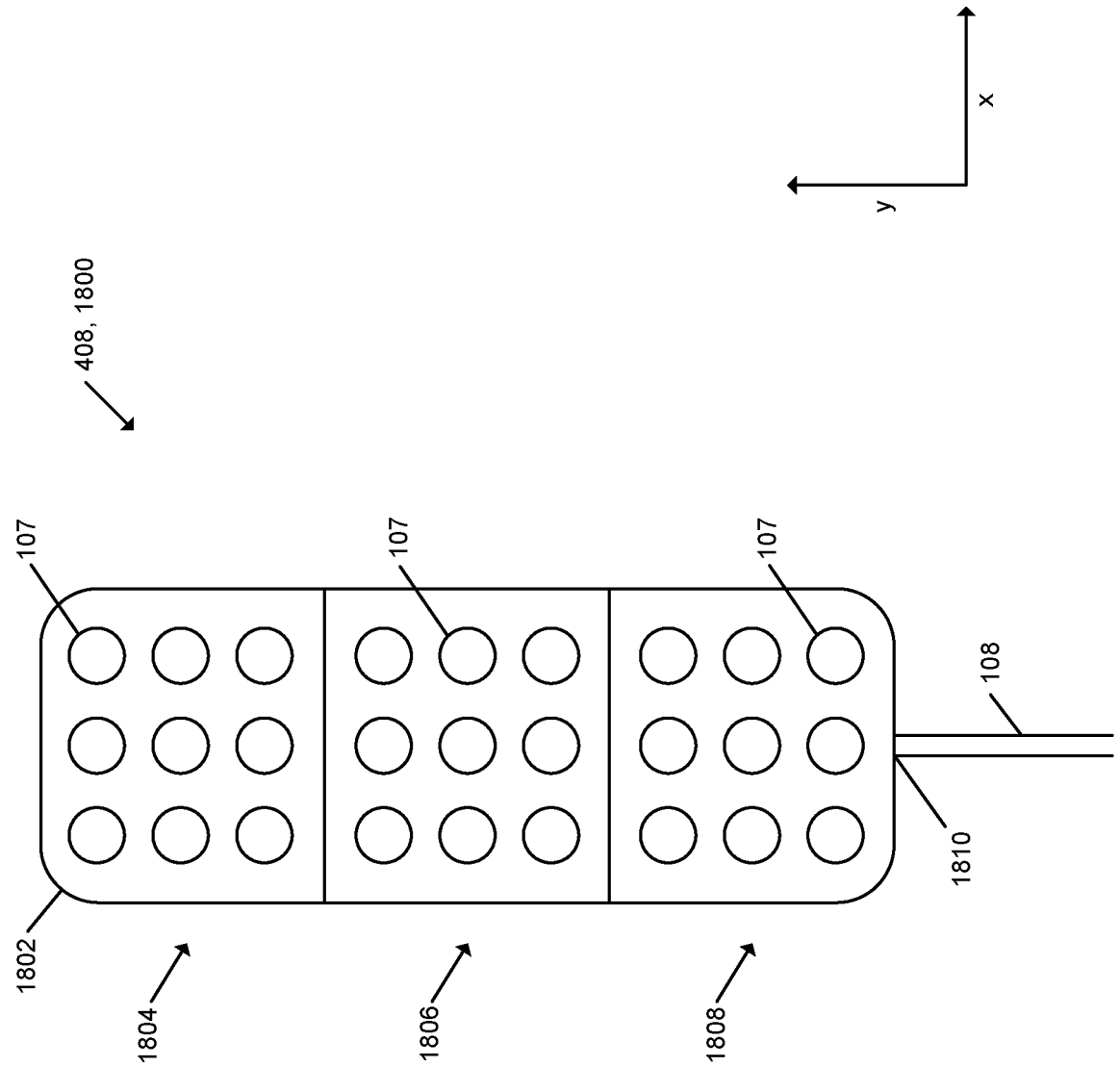
FIG. 18 illustrates at least one other embodiment of an electrode array of an electrical stimulation device.

Referring now to FIG. 18, at least one embodiment of an electrode array 1800 is shown as part of an electrode assembly 1802. As shown, the illustrative electrode array 1800 includes twenty-seven electrodes 107, which are divided into three groups of nine electrodes 107. Specifically, nine electrodes 107 are grouped together at a distal section 1804 of the electrode assembly 1802, nine electrodes 107 are grouped together at a central section 1806 of the electrode assembly 1802, and nine electrodes 107 are grouped together at a proximal section 1808 of the electrode assembly 1802. For clarity of the figure, only a subset of the twenty-seven electrodes 107 have been expressed labeled in FIG. 18; however, such designation is for reference only and not intended to convey a distinction. Similar conventions have been employed in FIGS. 19 and 20. Although the illustrative embodiment of the electrode array 1800 depicts twenty-seven electrodes 107, it should be appreciated that the electrode array 1800 may include a greater or lesser number of electrodes in other embodiments. Further, although the illustrative embodiment of the electrode array 1800 depicts three groups of electrodes 107 (i.e., sections 1804, 1806, 1808), it should be appreciated that the electrode array 1800 may include a greater or lesser number of sections in other embodiments. Additionally, it should be appreciated that the number of electrodes 107 in a particular section of the electrode array 1800 (e.g., sections 1804, 1806, 1808) may vary depending on the particular embodiment, and may differ between sections. For example, in some embodiments, section 1804 may include a different number of electrodes 107 from section 1806 and/or section 1808. Additionally, although the sections 1804, 1806, 1808 of the electrode assembly 1802 are described in reference to their distal/proximal location on the electrode assembly 1802, it should be appreciated that electrodes 107 may be otherwise grouped based on their locations in other embodiments. For example, in some embodiments, the electrode assembly 1802 may include medial and lateral sections and, therefore, corresponding groups of electrodes 107.

It should be appreciated that the electrode array 1800 (or, more specifically, the electrodes 107 thereof) may be electrically coupled to a signal generator 109 through a lead 108 as described herein. As shown, in the illustrative embodiment, the electrode assembly 1802 is relatively rectangular in cross-sectional shape, extending lengthwise and distally from a point of connection 1810 with the lead 108 (e.g., along a y-axis). However, it should be appreciated that the electrode assembly 1802 may be otherwise shaped in other embodiments (e.g., cylindrical). In the illustrative embodiment, each of the electrodes 107 has a circular cross-section and is spatially separated from the other electrodes 107 (e.g., to avoid electrical interference between electrodes 107 and/or other unwanted electrical/electromagnetic characteristics). In other embodiments, however, it should be appreciated that the lead 108 may otherwise connect with the electrode assembly 1802.

In use, in the illustrative embodiment, the controller 110 of the electrical stimulation system 400 is configured to randomly select a set of one or more electrodes 107 of the electrode array 1800 to function as electrical sources and a separate set of one or more electrodes 107 to function as electrical sinks. It should be appreciated that the remaining electrodes 107 that have not been selected to function as electrical sources or electrical sinks may remain off or otherwise non-functioning. Further, in some embodiments, the number of electrodes 107 selected as sources and/or the number of electrodes 107 selected as sinks may also be randomly determined. In some embodiments, the controller 110 may also randomly select the polarity of the assignment. Further, in some embodiments, the separation distance between electrodes 107 of opposite polarity may be specified.

Figure 19:
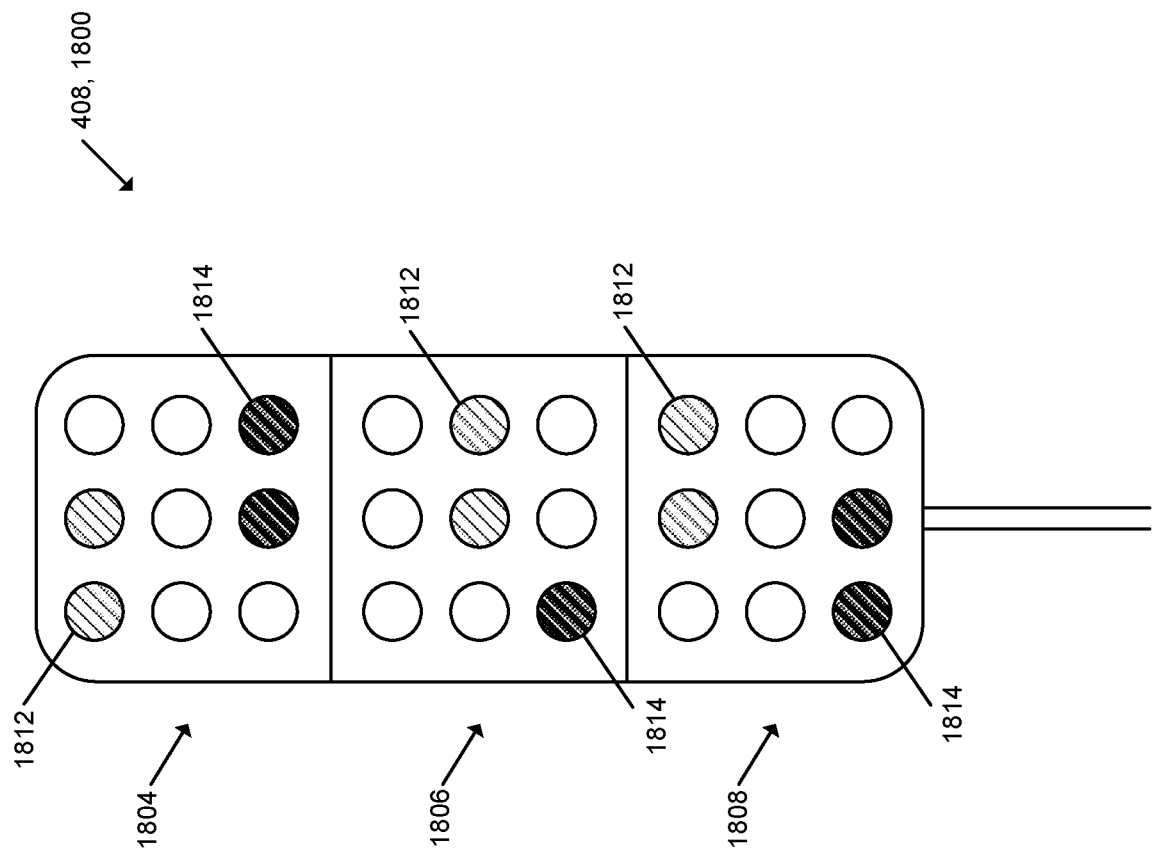
FIG. 19 illustrates one or more electrical configuration of the electrode array of FIG. 18.

By way of example, FIG. 19 illustrates various electrical configurations of the electrode array 1800 that could be randomly selected by the controller 110. FIG. 19 depicts at least one configuration in which the controller 110 has randomly selected two electrodes 107 in the distal section 1804 of the electrode array 1800 to be sources 1812, two electrodes 107 in the central section 1806 of the electrode array 1800 to be sources 1812, two electrodes 107 in the proximal section 1808 of the electrode array 1800 to be sources 1812, two electrodes 107 in the distal section 1804 of the electrode array 1800 to be sinks 1814, one electrode 107 in the central section 1806 of the electrode array 1800 to be a sink 1814, and two electrodes 107 in the proximal section 1808 of the electrode array 1800 to be sinks. Although each of the sources 1812 and sinks 1814 is not separately labeled in FIG. 19, for clarity, each of the sources 1812 is depicted in FIG. 19 as having the same fill pattern and each of the sinks 1814 is depicted in FIG. 19 as having a different fill pattern.

In some embodiments, the electrical stimulation and/or electrode assignments and configuration may be adjusted (or tuned) with respect to each of the sections 1804, 1806, 1808 of the electrode array 1800. For example, the stimulation parameter (e.g., amplitude, frequency, pulse duration, charge per phase, etc.) and/or electrode assignment/selection delivered to each section 1804, 1806, 1808 may be tuned based on feedback. For example, in some embodiments, the distal section 1804 of the electrode array 1800 may be restricted to delivering high frequency signals (or high-frequency components of the electrical stimulation signals), whereas the central section 1806 and the proximal section 1808 may be restricted to delivering moderate and low frequency signals (or moderate- and low-frequency components of the electrical stimulation signals). In another embodiment, the central section 1806 may be restricted to delivering moderate frequency signals (or moderate-frequency components of the electrical stimulation signals) and the proximal section 1808 may be restricted to delivering low frequency signals (or low-frequency components of the electrical stimulation signals).

In another embodiment, the amplitude of the electrical stimulation signal being delivered may be independently adjusted or weighted for each of the sections 1804, 1806, 1808 of the electrode array 1800. For example, in an embodiment, the amplitude of the electrical stimulation signal being delivered to the distal section 1804 of the electrode array 1800 may be amplified/weighted by a factor of 2.0 (i.e., doubled), the amplitude of the electrical stimulation signal being delivered to the central section 1806 of the electrode array 1800 may be amplified/weighted by a factor of 0.5 (i.e., attenuated by one half), and the amplitude of the electrical stimulation signal being delivered to the proximal section 1808 of the electrode array 1800 may be amplified/weighted by a factor of 1.0 (i.e., passed through). Although the independent adjustment/weighting of the amplitude of the electrical stimulation signal is described herein as being done with respect to different sections 1804, 1806, 1808 of the electrode array 1800, it should be appreciated that the amplitude of the electrical stimulation signal may be independently adjusted/weighted for each electrode 107 or other set(s) of electrodes 107 in other embodiments.

Figure 20:
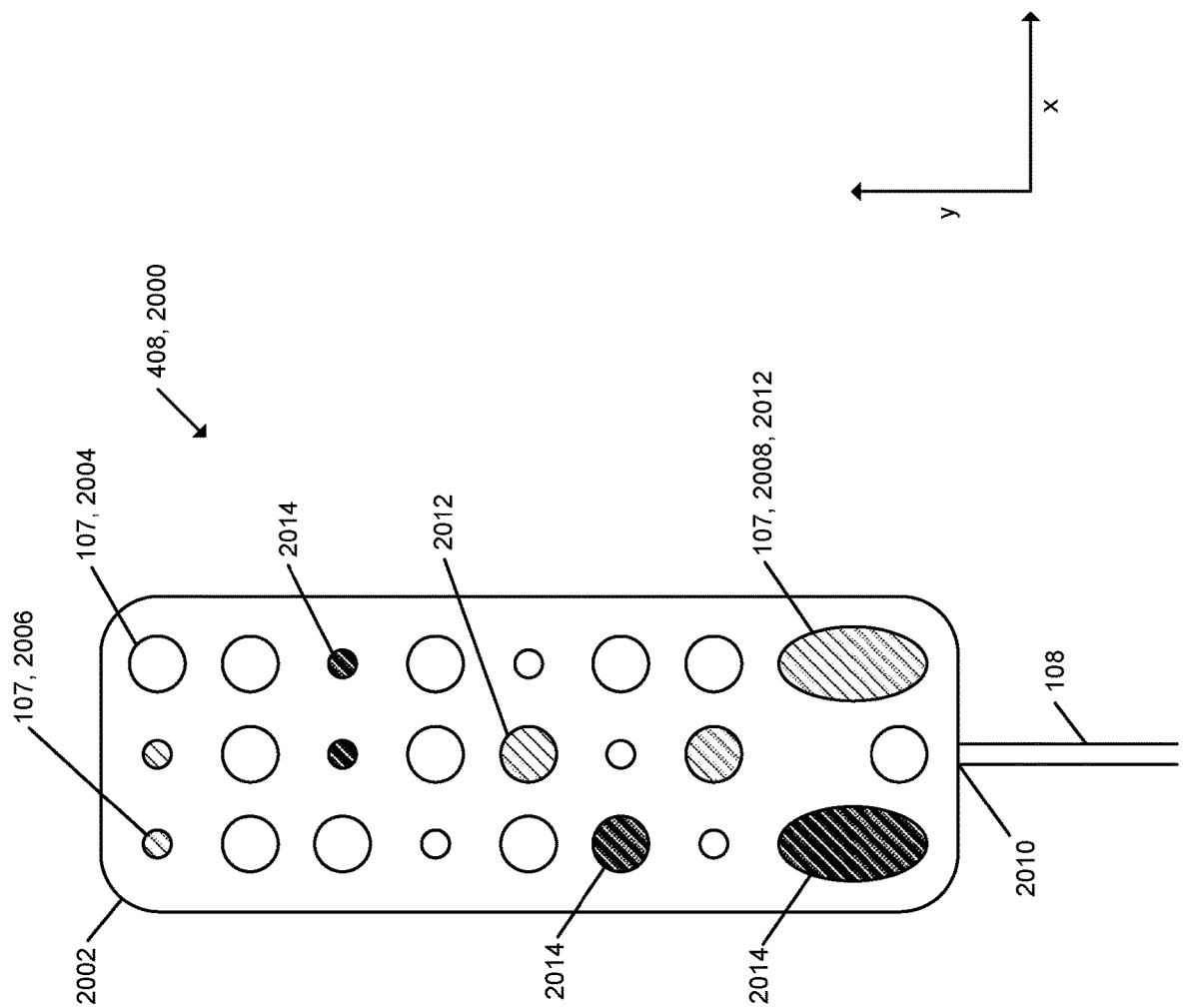
FIG. 20 illustrates at least one other embodiment of an electrode array of an electrical stimulation device and one or more electrical configurations thereof.

Referring now to FIG. 20, at least one embodiment of an electrode array 2000 is shown as part of an electrode assembly 2002. As shown, the illustrative electrode array 2000 includes twenty-four electrodes 107 of varying sizes and shapes. Specifically, the electrode array 2000 includes fourteen electrodes 107, 2004 that have a circular cross-section and are of a first size, eight electrodes 107, 2006 that have a circular cross-section and are of a second size (i.e., smaller than the first size), and two electrodes 107, 2008 that have an elliptical/oval cross-section and are of a third size (i.e., larger than the first size). Although the illustrative embodiment of the electrode array 2000 depicts twenty-four electrodes 107, it should be appreciated that the electrode array 2000 may include a greater or lesser number of electrodes in other embodiments. Further, although the illustrative embodiment of the electrode array 2000 depicts three different sizes/shapes of electrodes 107 (i.e., electrodes 2004, 2006, 2008), it should be appreciated that the electrode array 2000 may include a greater or lesser number of different sizes/shapes in other embodiments. Additionally, it should be appreciated that the number of electrodes 107 of a particular size/shape in the electrode array 2000 may vary depending on the particular embodiment.

It should be appreciated that the electrode array 2000 (or, more specifically, the electrodes 107 thereof) may be electrically coupled to a signal generator 109 through a lead 108 as described herein. As shown, in the illustrative embodiment, the electrode assembly 2002 is relatively rectangular in cross-sectional shape, extending lengthwise and distally from a point of connection 2010 with the lead 108 (e.g., along a y-axis). However, it should be appreciated that the electrode assembly 2002 may be otherwise shaped in other embodiments (e.g., cylindrical). In the illustrative embodiment, each of the electrodes 107 is spatially separated from the other electrodes 107 (e.g., to avoid electrical interference between electrodes 107 and/or other unwanted electrical/electromagnetic characteristics). In other embodiments, however, it should be appreciated that the lead 108 may otherwise connect with the electrode assembly 2002.

In use, in the illustrative embodiment, the controller 110 of the electrical stimulation system 400 is configured to randomly select a set of one or more electrodes 107 of the electrode array 2000 to function as electrical sources and a separate set of one or more electrodes 107 to function as electrical sinks. It should be appreciated that the remaining electrodes 107 that have not been selected to function as electrical sources or electrical sinks may remain off or otherwise non-functioning. Further, in some embodiments, the number of electrodes 107 selected as sources and/or the number of electrodes 107 selected as sinks may also be randomly determined. In some embodiments, the controller 110 may also randomly select the polarity of the assignment.

By way of example, FIG. 20 illustrates at least one electrical configuration of the electrode array 2000 that could be randomly selected by the controller 110. More specifically, FIG. 20 depicts at least one configuration in which the controller 110 has randomly selected two of the electrodes 107, 2004 that have a circular cross-section and are of the first size as sources 2012, one of the electrodes 107, 2004 that have a circular cross-section and are of the first size as a sink 2014, two of the electrodes 107, 2006 that have a circular cross-section and are of the second size as sources 2012, two of the electrodes 107, 2006 that have a circular cross-section and are of the second size as sinks 2014, one of the electrodes 107, 2008 that have an elliptical/oval cross-section and are of the third size as a source 2012, and one of the electrodes 107, 2008 that have an elliptical/oval cross-section and are of the third size as a sink 2014. Although each of the sources 2012 and sinks 2014 is not separately labeled in FIG. 20, for clarity, each of the sources 2012 is depicted in FIG. 20 as having the same fill pattern and each of the sources 2014 is depicted in FIG. 20 as having a different fill pattern.

It should be appreciated that the sizes and shapes of the electrodes 107 depicted in FIG. 20 are for illustrative purposes. Therefore, in various embodiments, a particular electrode array 408 may be designed to have different sized and/or shaped (e.g., circular, elliptical/oval, square, rectangular, polygonal, etc.) electrodes 107. Further, in various embodiments, the electrodes 107 of the electrode array 408 may be composed of one or more materials (e.g., platinum, carbon, stainless steel, P-dot coated, roughed surface), which may vary among electrodes 107 in a particular electrode array 408. In some embodiments, the electrical stimulation and/or electrode assignments and configuration may be adjusted (or tuned) with respect to the size, shape, and/or material of the various electrodes 107 of the electrode array 408. For example, in some embodiments, low frequency signals (or low-frequency components of the electrical stimulation signals) may be restricted to being delivered through the largest electrodes 107 or the electrodes 107 with enhanced charge capacity characteristics, whereas the higher frequency signals (or higher-frequency components of the electrical stimulation signals) may be delivered on smaller sized electrodes 107 (or larger electrodes 107).

Figure 21:
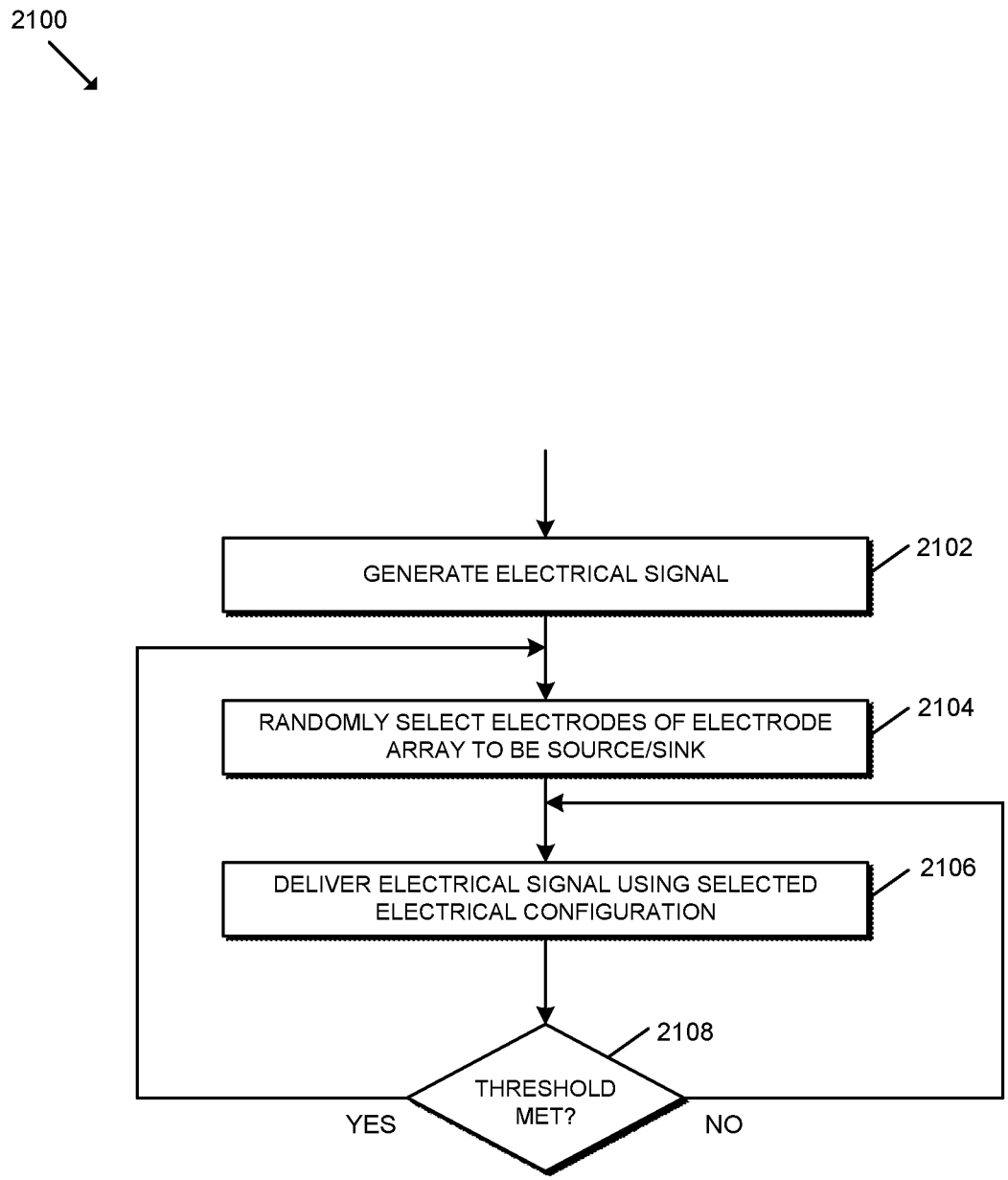
FIG. 21 is a simplified flow diagram of at least one embodiment of a method of randomly selecting an electrical configuration of an electrode array for delivering electrical stimulation to a patient.

Referring now to FIG. 21, in use, the electrical stimulation system 400 may execute a method 2100 for randomly selecting an electrical configuration of an electrode array for delivering electrical stimulation to a patient. It should be appreciated that the particular blocks of the method 2100 are illustrated by way of example, and such blocks may be combined or divided, added or removed, and/or reordered in whole or in part depending on the particular embodiment, unless stated to the contrary.

The illustrative method 2100 begins with block 2102 in which the electrical stimulation system 400 or, more specifically, the signal generator 109 generates an electrical stimulation signal (e.g., in response to instructions from the controller 110). As described above, in various embodiments, the electrical stimulation signal may be a periodic signal, aperiodic signal, impulses, pulses, direct current waveform, noise signal, and/or another waveform (e.g., 0-1 MHz). For example, in some embodiments, the electrical stimulation signal may have a frequency range of 0.05 Hz to 750 kHz. More specifically, in some embodiments, the electrical stimulation signal may have a frequency range of 0.05 Hz to 2 kHz, which blocks the action potential from even firing. In another embodiment, the electrical stimulation signal may have a frequency range of 10 kHz to 16 kHz, which stimulates the nerve so that it attenuates or prevents the nerve from firing a pain signal. In yet another embodiment, the electrical stimulation signal may have a frequency range of 500 kHz to 750 kHz, which results in so much energy around the nerve that it causes the nerve cell to run out of its mitochondrial stores of energy. In other words, such an electrical stimulation signal may fatigue the nerve, so that it essentially becomes tired and is unable to fire. As such, the electrical stimulation system 400 is able to deliver the signal to the patient for a period (e.g., five minutes), turn the stimulation off for an extended period (e.g., several days) while the nerve cells rebuild their mitochondrial stores, and again deliver the signal to the patient to again fatigue the nerve and deplete the stores. It has been discovered that delivering the electrical stimulation signal within this frequency range for approximately five minutes may block the nerve for approximately twenty-one days. Accordingly, it should be appreciated that the mechanism of action of the electrical stimulation signal that is randomly distributed across the electrodes 107 of the electrode array 408 may vary depending on the particular frequency range of the signal. In alternative embodiments, the electrical stimulation signal may have a frequency range of 1 kHz to 100 kHz, or the electrical stimulation signal may have a frequency range of 100 kHz to 1 MHz. It should be appreciated that the frequency range of 100 kHz to 1 MHz may selectively inhibit the parts of the nerve responsible for normal pain and autonomic function. The time-course of these effects have been demonstrated to last days-to-weeks (e.g., 21 days post-treatment) when healthy neuronal circuitry is simulated, and weeks-to-months when stimulation is delivered to diseased neural circuitry (e.g., hosting chronic pain).

In block 2104, the electrical stimulation system 400 (e.g., the controller 110) randomly selects one or more electrodes 107 of the electrode array 408 to function as electrical sources and one or more other electrodes 107 of the electrode array 408 to function as electrical sinks. As described above, it should be appreciated that the number of electrodes 107 selected as electrical sources and/or the number of electrodes 107 selected as electrical sinks may also be randomly determined. Further, in some embodiments, the polarity of the assignment may also be randomly selected. In block 2106, the electrical stimulation system 400 (e.g., the signal generator 109 by virtue of instructions received from the controller 110) delivers the electrical stimulation signal to the patient through the electrode array 408 using the randomly selected electrical configuration. As indicated above, in some embodiments, it should be appreciated that various frequency components (e.g., high-, low-, or moderate-frequency components) of the electrical stimulation signal may further be directed to pass through a subset of the randomly selected electrodes of the electrode array 408. Further, in some embodiments, the source electrode(s) 107 and sink electrode(s) 107 may be selected based on stimulus feature (e.g., frequency, amplitude, charge density, time, pulse number, etc.). For example, certain features/components of the electrical stimulation signal (e.g., a particular frequency range, amplitude, etc.) may be delivered to the patient through one set of electrode(s) 107, whereas other features/components of the electrical stimulation signal may be delivered to the patient through another set of electrode(s) 107.

As indicated above, in some embodiments, a particular electrical stimulation signal is only delivered to the patient through the selected electrical configuration of source electrode(s) 107 and sink electrode(s) 107 for a threshold period of time (or until another threshold is met), which may be measured using various techniques. Accordingly, in block 2108, the electrical stimulation system 400 determines whether the threshold has been met. If not, the method 2100 returns to block 2106 in which the electrical stimulation system 400 continues to deliver the electrical stimulation signal through the selected electrical configuration. However, if the threshold has been met, the method 2100 returns to block 2104 in which the electrical stimulation system 400 randomly selects a new set of one or more electrodes 107 of the electrode array 408 to function as electrical sources and one or more other electrodes 107 of the electrode array 408 to function as electrical sinks. In other words, the electrical stimulation system 400 periodically updates the randomly selected set of source electrode(s) 107 and sink electrode(s) 107 through which the electrical stimulation signal is transmitted, for example, in order to ensure that the signal is delivered to the patient's tissue in a spatially random way.

Although the blocks 2102-2108 are described in a relatively serial manner, it should be appreciated that various blocks of the method 2100 may be performed in parallel in some embodiments.

Figure 22:
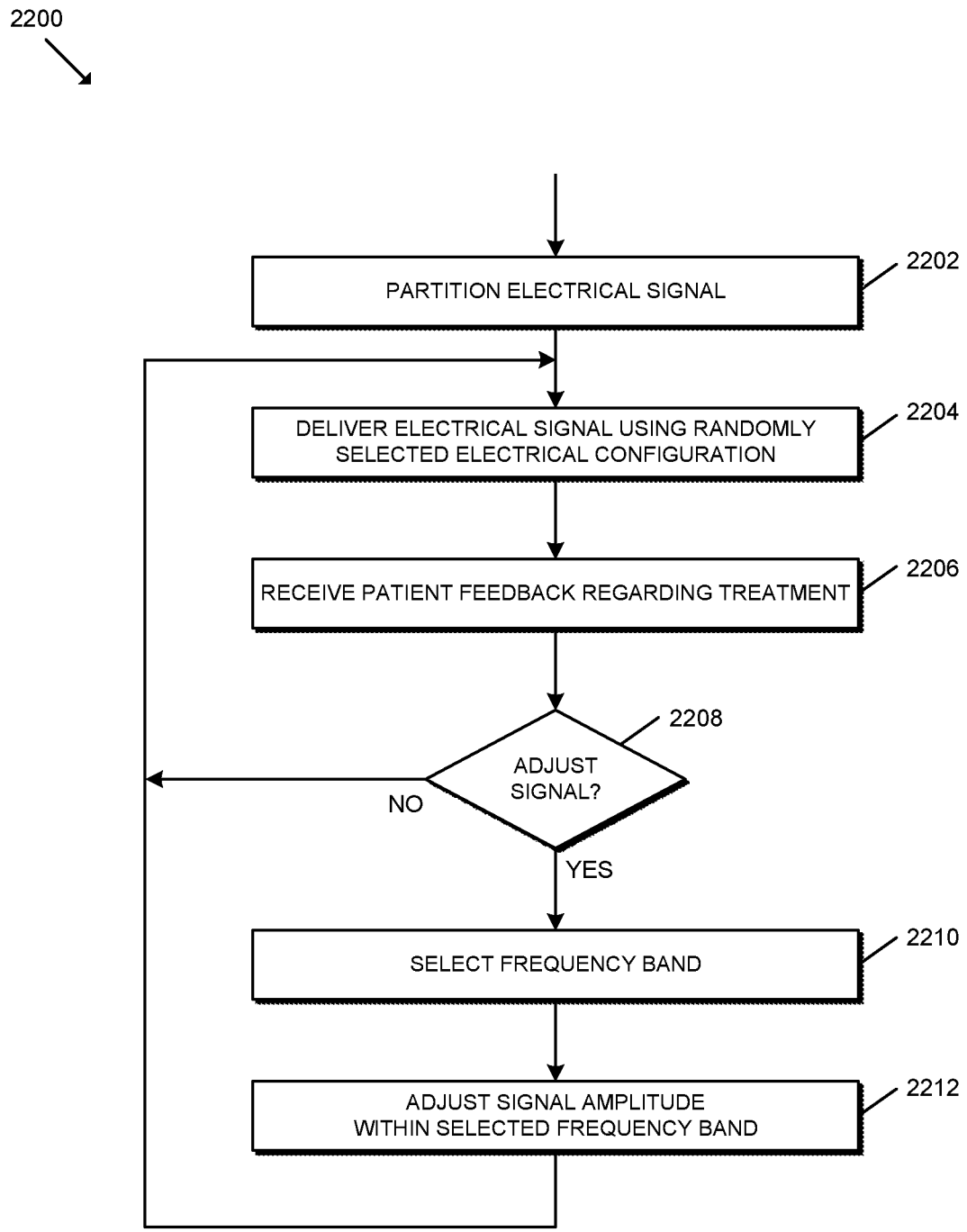
FIG. 22 is a simplified flow diagram of at least one embodiment of a method of providing spatially random electrical stimulation to a patient.

Referring now to FIG. 22, in use, the electrical stimulation system 400 may execute a method 2200 for providing spatially random electrical stimulation to a patient. It should be appreciated that the particular blocks of the method 2200 are illustrated by way of example, and such blocks may be combined or divided, added or removed, and/or reordered in whole or in part depending on the particular embodiment, unless stated to the contrary. It should be further appreciated that the method 2200 of FIG. 22 may be executed in conjunction with (e.g., in parallel with) the method 2100 of FIG. 21 described above.

Figure 23:
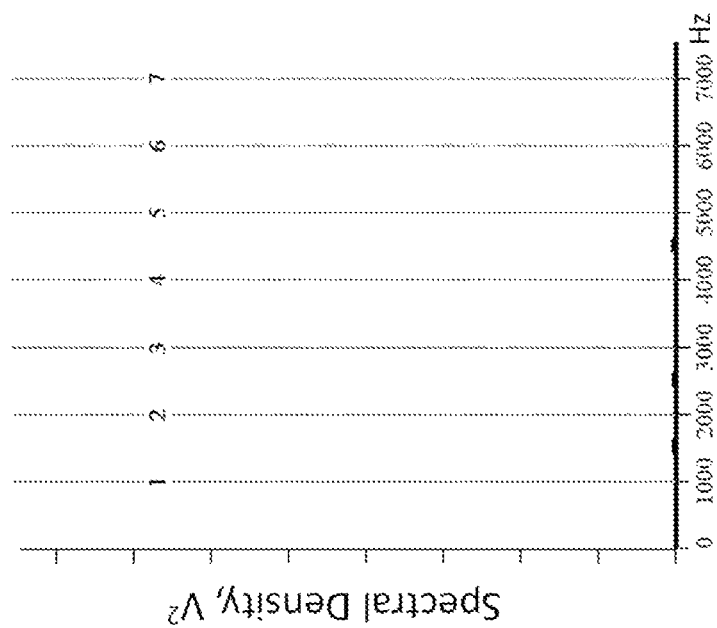
FIG. 23 is a graph that illustrates partitioned frequency bands of at least a portion of a frequency range of an electrical signal.
Figure 24:
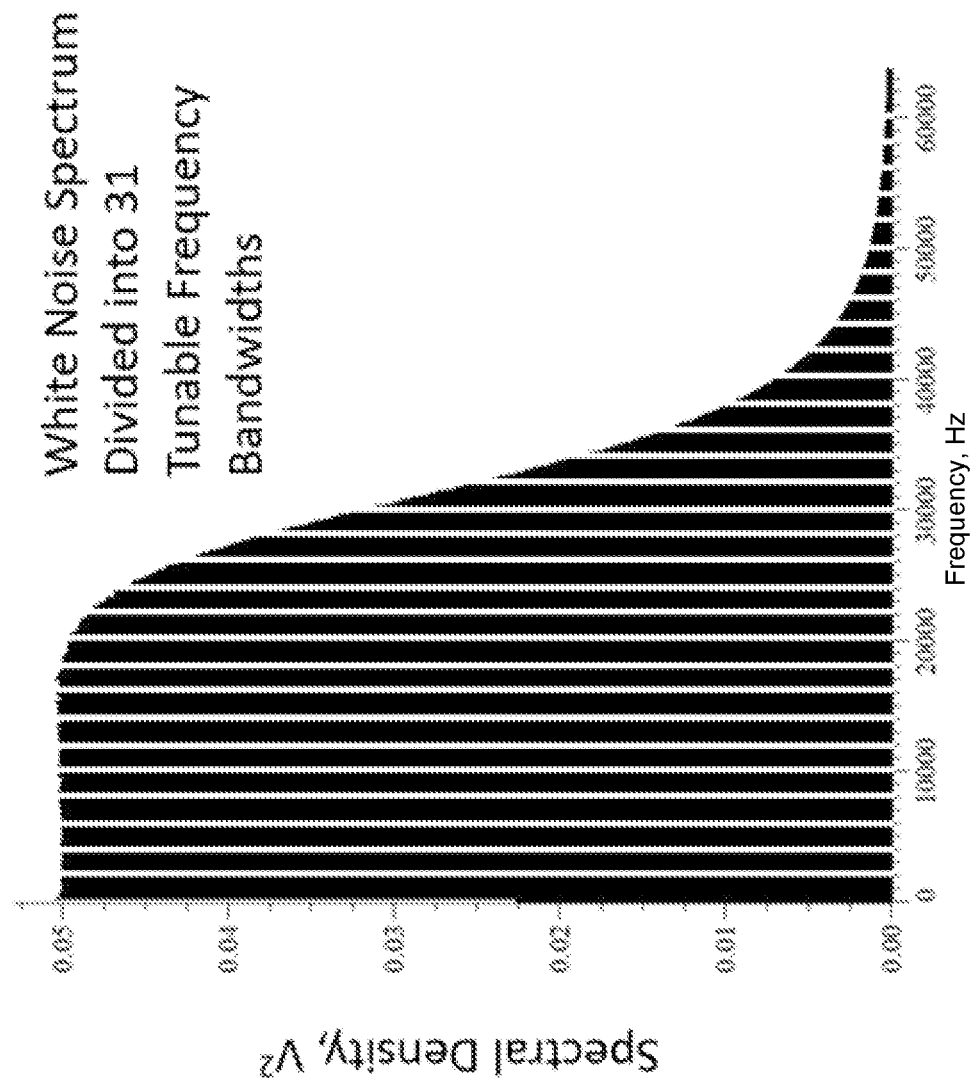
FIG. 24 is a graph of the power spectrum of a broad spectrum electrical noise signal that has been partitioned into discrete frequency bands.

The illustrative method 2200 begins with block 2202 in which the electrical stimulation system 400 (e.g., the controller 110) partitions a frequency range into discrete frequency bands. For example, in an embodiment, the frequencies range may be from 0 to 100,000 Hz in equally spaced linear frequency bands (e.g., 1,000 Hz, 2,500 Hz, etc.). By way of example, FIG. 23 depicts a frequency range of a periodic signal that is partitioned into discrete frequency bands that have 1,000 Hz bandwidths. In another example, FIG. 24 depicts a broad spectrum electrical noise signal that has been partitioned/divided into 31 discrete tunable frequency bandwidths. It should be appreciated that the size of the bandwidths may differ depending on the particular embodiment. Further, although each of the bandwidths are described herein and depicted in FIGS. 23 and 24 as having the same width, it should be appreciated that one or more of the partitioned frequency bandwidths may have a different width from others in other embodiments. In an embodiment, each of the frequency bands in a frequency range of 0 Hz to 100 kHz of the partitioned spectrum has a bandwidth of one of 1 kHz or 2 kHz. Accordingly, it should be appreciated that the size of the bandwidths may different depending on the particular embodiment. Additionally, the bandwidths may have the same or different widths depending on the particular embodiment. In some embodiments, the frequency may be described on a logarithmic scale and described by base2 (e.g., octaves: 10 Hz, 20 Hz, 40 Hz, 80 Hz, 160 Hz, 320 Hz, 640 Hz, 1280 Hz, 2560 Hz, etc.) and/or base-10 (e.g., 10 Hz, 100 Hz, 1,000 Hz, 10,000 Hz, 100,000 Hz, etc.) axis, with bandwidths described a Q-factor (center frequency/bandwidth) or bandwidth: octaves (1/10 to 10 oct).

In block 2204, the electrical stimulation system 400 (e.g., the signal generator 109) delivers the electrical stimulation signal through the randomly selected electrodes 107 of the electrode array 408 using the randomly selected electrical configuration of electrical sources and electrical sinks as described above.

In block 2206, the electrical stimulation system 400 and/or the clinician receives feedback regarding the treatment from the patient. As described above, it should be appreciated that the feedback can be provided by the patient, for example, based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof. In some embodiments, the electrical stimulation signal(s) can be adjusted based on patient feedback describing unwanted sensations. Examples of unwanted sensations include pain and other sensations, such as urinary urgency and fecal urgency. Other examples include unwanted sensations of touch, vibration, pressure, tightness, feelings of warmth or cold, numbness, sounds of ringing (or buzzing, hissing, clicking, roaring, humming), anxiety, dizziness, aura, loss of sound intensity, and/or loss of sound quality. Any of the unwanted sensations described above can occur in the absence of an external stimulus and/or when the patient is perfectly still. Further, in some embodiments, the electrical stimulation signal(s) can be adjusted based on patient feedback describing physiological outcomes. It should be appreciated that the physiological outcomes may be reported by the patient, observed by a clinician, evaluated based on data generated by one or more sensors, and/or otherwise determined depending on the particular embodiment. Examples of physiological outcomes that can be used to adjust the electrical signals include those pertaining to bladder and bowel function, such as incontinence, constipation, voided volumes, voiding pressures, voiding frequency, and electromyogram signals of the urinary and colonic ensemble. Other examples of physiological outcomes that can be used to adjust the electrical signals include those pertaining to motor function, such as electromyogram signals, strength, weakness, stiffness, spasm, contracture, tremors, spasticity, atrophy, bradykinesia, and paralysis. Other markers of physiological activity that could be used to adjust the electrical signals include electroencephalogram signals, evoked brain potentials, and cognitive changes including dementia, hallucination, and delusion. Markers of autonomic function can also be used to adjust the electrical signals, such as heart-rate, blood flow, blood pressure, respiration, nausea, sweat production, skin color, and edema. Any of the physiological changes described above can be used to adjust the electrical signals in the absence of an external stimulus or when the patient is perfectly still. In some embodiments, sensor types include biopotential electrodes, pressure sensors and flow meters, chemical sensors, and/or temperature sensors (e.g., thermistors). It should be appreciated that, in some embodiments, one or more of the sensors can act in a close-loop fashion to adjust the electrical signals to provide and optimize therapy.

In block 2206, the electrical stimulation system 400 and/or the clinician determines whether to further adjust the signal applied to the patient based on the patient feedback (e.g., in an effort to most optimally alleviate the patient's condition). If not, the method 2200 returns to block 2204 in which the electrical stimulation system 400 (e.g., the signal generator 109) delivers the electrical stimulation signal through the randomly selected electrodes 107 of the electrode array 408 using the randomly selected electrical configuration of electrical sources and electrical sinks. However, it should be appreciated that, in some circumstances, the particular randomly selected electrical configuration of electrical sources and electrical sinks may have changed relative to the prior execution of block 2204 due to the execution of the method 2100 of FIG. 21 described above in conjunction with the execution of the method 2200 of FIG. 22.

However, if in block 2206, the electrical stimulation system 400 and/or the clinician determines to adjust the signal applied to the patient based on the patient feedback (e.g., in an effort to most optimally alleviate the patient's condition), the method 2200 advances to block 2210 in which the electrical stimulation system 400 selects a particular frequency band of the discretely partitioned frequency bands for adjustment. In some embodiments, selection of the particular frequency band may involve selecting a corresponding signal generator 109 (in the case of multiple signal generators 109), for example, in an embodiment in which each frequency band is powered by a different signal generator 109. In block 2212, the electrical stimulation system 400 adjusts the amplitude of the voltage and/or current of the signal within the selected frequency band, for example, by amplifying the voltage and/or current of the signal within that particular frequency band or attenuating the voltage and/or current of the signal within that particular frequency band. It should be appreciated that the amount of amplification/attenuation of the signal may be user-controlled, predefined, and/or otherwise determined depending on the particular embodiment. It should be appreciated that, in the illustrative embodiment, the clinician and/or patient may select and/or adjust the frequency band using one or more user interface 112 devices. However, the frequency band may be otherwise selected in other embodiments. In other embodiments, the electrical stimulation system 400 may additionally or alternatively adjust the phase and/or frequency of the periodic waveform corresponding with the selected frequency band in order to tune the patient.

The method 2200 returns to block 2204 in which the electrical stimulation system 400 (e.g., the signal generator 109) delivers the electrical stimulation signal through the randomly selected electrodes 107 of the electrode array 408 using the randomly selected electrical configuration of electrical sources and electrical sinks. As indicated above, it should be appreciated that, in some circumstances, the particular randomly selected electrical configuration of electrical sources and electrical sinks may have changed relative to the prior execution of block 2204 due to the execution of the method 2100 of FIG. 21 described above in conjunction with the execution of the method 2200 of FIG. 22. It should be further appreciated that the method 2200 allows for the patient and/or clinician to independently adjust the amplitude of the voltage and/or current of the electrical stimulation signal within multiple frequency bands (e.g., each frequency band) of that signal, such that the electrical stimulation signal is adjusted for optimal (or improved) treatment of the patient's condition. In some embodiments, the adjusted signal may be delivered to the patient continuously or intermittently (e.g., with durations of less than thirty minutes).

Although the blocks 2202-2212 are described in a relatively serial manner, it should be appreciated that various blocks of the method 2200 may be performed in parallel in some embodiments.

What is claimed is:

1. An electrical stimulation system for delivering spatially random electrical stimulation to a patient through an electrode array during electrical stimulation therapy of the patient, the electrical stimulation system comprising:

an electrode array comprising a plurality of electrodes spaced apart from one another;

a signal generator electrically coupled to the electrode array and configured to deliver an electrical stimulation signal; and a controller comprising a processor and a memory having a plurality of instructions stored thereon that, in response to execution by the processor, causes the controller to:

randomly select, at periodic intervals based on a predefined period of time, an electrical configuration from the plurality of electrodes of the electrode array during the electrical stimulation therapy, wherein to randomly select the electrical configuration comprises to randomly select a first set of electrodes of the plurality of electrodes to function as electrical sources and a second set of electrodes of the plurality of electrodes, different from the first set of electrodes, to function as electrical sinks; and instruct the signal generator to deliver the electrical stimulation signal to the patient for the predefined period of time via the randomly selected electrical configuration to improve a condition of the patient;

wherein the plurality of electrodes comprises a third set of electrodes of a first size and a fourth set of electrodes of a second size greater than the first size;

wherein the plurality of instructions further causes the controller to select each of the third set of electrodes and the fourth set of electrodes based on an electrode size;

wherein the signal generator is configured to deliver high-frequency signal components of the electrical stimulation signal through only the third set of electrodes; and wherein the signal generator is configured to deliver low-frequency signal components of the electrical stimulation signal through only the fourth set of electrodes.

2. The electrical stimulation system of claim 1, wherein the plurality of instructions further causes the controller to randomly assign a polarity to one or more of the electrodes of the first set of electrodes and the second set of electrodes.

3. The electrical stimulation system of claim 1, wherein the electrical stimulation signal comprises a noise signal.

4. The electrical stimulation system of claim 1, wherein the plurality of instructions further causes the controller to:

partition a frequency range of the electrical stimulation signal into a plurality of discrete frequency bands, each of the discrete frequency bands having a corresponding bandwidth;

adjust an amplitude of one or more of a voltage or a current of the electrical stimulation signal within a selected frequency band of the plurality of discrete frequency bands to generate an adjusted electrical signal based on feedback received from the patient; and instruct the signal generator to deliver the adjusted electrical signal to the patient via the randomly selected electrical configuration.

5. The electrical stimulation system of claim 4, wherein the feedback comprises at least one of feedback received from the patient as patient self-report regarding the therapy delivered to the patient, feedback based on data generated by one or more sensors of the electrical stimulation system, wherein the one or more sensors measure one or more physiological outcomes of the patient, or feedback data received from a machine learning system.

6. An electrical stimulation system for delivering spatially random electrical stimulation to a patient through an electrode array, the electrical stimulation system comprising:

an electrode array comprising a plurality of electrodes spaced apart from one another;

a signal generator electrically coupled to the electrode array and configured to deliver an electrical stimulation signal; and a controller comprising a processor and a memory having a plurality of instructions stored thereon that, in response to execution by the processor, causes the controller to:

randomly select an electrical configuration from the plurality of electrodes of the electrode array, wherein to randomly select the electrical configuration comprises to randomly select a first set of electrodes of the plurality of electrodes to function as electrical sources and a second set of electrodes of the plurality of electrodes, different from the first set of electrodes, to function as electrical sinks; and instruct the signal generator to deliver the electrical stimulation signal to the patient via the randomly selected electrical configuration;

wherein the plurality of electrodes comprises a third set of electrodes and a fourth set of electrodes different from the third set of electrodes; and wherein to instruct the signal generator to deliver the electrical stimulation signal to the patient via the randomly selected electrical configuration comprises to instruct the signal generator to deliver a first set of features of the electrical stimulation signal to the patient via the third set of electrodes and a second set of features of the electrical stimulation signal, different from the first set of features, to the patient via the fourth set of electrodes;

wherein the plurality of instructions further causes the controller to select each of the third set of electrodes and the fourth set of electrodes based on an electrode size;

wherein the third set of electrodes includes electrodes of a first size and the fourth set of electrodes includes electrodes of a second size greater than the first size;

wherein the signal generator is configured to deliver high-frequency signal components of the electrical stimulation signal through only the third set of electrodes; and wherein the signal generator is configured to deliver low-frequency signal components of the electrical stimulation signal through only the fourth set of electrodes.

7. The electrical stimulation system of claim 6, wherein the plurality of instructions further causes the controller to select each of the third set of electrodes and the fourth set of electrodes based on an electrode location on an electrode assembly; and wherein the electrode array comprises at least a distal section and a proximal section.

8. The electrical stimulation system of claim 7, wherein the signal generator is configured to amplify signals transmitted through each electrode located on the distal section at a different weight from signals transmitted through each electrode located on the proximal section.

9. The electrical stimulation system of claim 6, wherein the plurality of instructions further causes the controller to select each of the third set of electrodes and the fourth set of electrodes based on an electrode shape; and wherein the third set of electrodes includes electrodes of a first cross-sectional shape and the fourth set of electrodes includes electrodes of a second cross-sectional shape different from the first cross-sectional shape.

10. The electrical stimulation system of claim 6, wherein the plurality of instructions further causes the controller to select each of the third set of electrodes and the fourth set of electrodes based on an electrode material.

11. The electrical stimulation system of claim 10, wherein the third set of electrodes includes electrodes composed of a first material and the fourth set of electrodes includes electrodes composed of a second material different from the first material.

12. The electrical stimulation system of claim 6, wherein each of the third set of electrodes and the fourth set of electrodes is selected based on an electrode size, an electrode shape, an electrode material, and an electrode location on an electrode assembly.

13. The electrical stimulation system of claim 6, wherein to deliver the first set of features of the electrical stimulation signal to the patient via the third set of electrodes comprises to deliver components of the electrical stimulation signal having a first set of amplitudes to the patient via the third set of electrodes; and wherein to deliver the second set of features of the electrical stimulation signal to the patient via the fourth set of electrodes comprises to deliver components of the electrical stimulation signal having a second set of amplitudes, different from the first set of amplitudes, to the patient via the fourth set of electrodes.

14. The electrical stimulation system of claim 6, wherein to deliver the first set of features of the electrical stimulation signal to the patient via the third set of electrodes comprises to deliver components of the electrical stimulation signal having a first set of charge densities to the patient via the third set of electrodes; and wherein to deliver the second set of features of the electrical stimulation signal to the patient via the fourth set of electrodes comprises to deliver components of the electrical stimulation signal having a second set of charge densities, different from the first set of charge densities, to the patient via the fourth set of electrodes.

15. An electrical stimulation system for delivering spatially random electrical stimulation to a patient through an electrode array during electrical stimulation therapy of the patient, the electrical stimulation system comprising:

an electrode array comprising a plurality of electrodes spaced apart from one another;

a signal generator electrically coupled to the electrode array and configured to deliver an electrical stimulation signal; and a controller comprising a processor and a memory having a plurality of instructions stored thereon that, in response to execution by the processor, causes the controller to:

randomly select an electrical configuration from the plurality of electrodes of the electrode array during the electrical stimulation therapy, wherein to randomly select the electrical configuration comprises to randomly select a first set of electrodes of the plurality of electrodes to function as electrical sources and a second set of electrodes of the plurality of electrodes, different from the first set of electrodes, to function as electrical sinks;

instruct the signal generator to deliver the electrical stimulation signal to the patient via the randomly selected electrical configuration to improve a condition of the patient; and randomly select a new electrical configuration from the plurality of electrodes of the electrode array in response to a determination that a threshold period of time has been met;

wherein the plurality of electrodes comprises a third set of electrodes and a fourth set of electrodes different from the third set of electrodes; and wherein the plurality of instructions further causes the controller to select each of the third set of electrodes and the fourth set of electrodes based on an electrode size;

wherein the third set of electrodes includes electrodes of a first size and the fourth set of electrodes includes electrodes of a second size greater than the first size;

wherein the signal generator is configured to deliver high-frequency signal components of the electrical stimulation signal through only the third set of electrodes; and wherein the signal generator is configured to deliver low-frequency signal components of the electrical stimulation signal through only the fourth set of electrodes.

16. The electrical stimulation system of claim 15, wherein the threshold period of time is associated with an amount of charge of the spatially random electrical stimulation delivered to the patient injected by electrodes of the randomly selected electrical configuration.

17. The electrical stimulation system of claim 15, wherein the threshold period of time is based on a charge per pulse of the spatially random electrical stimulation being delivered to the patient.

18. The electrical stimulation system of claim 15, wherein the threshold period of time is based on a charge density of the spatially random electrical stimulation being delivered to the patient.

19. The electrical stimulation system of claim 15, wherein the threshold period of time is based on a previous stimulation history of the patient.

* * * * *